US006943168B2

(12) United States Patent
Snutch et al.

(10) Patent No.: US 6,943,168 B2
(45) Date of Patent: Sep. 13, 2005

(54) CALCIUM CHANNEL INHIBITORS COMPRISING BENZHYDRIL SPACED FROM PIPERAZINE

(75) Inventors: Terrance P. Snutch, Vancouver (CA);
Gerald W. Zamponi, Calagary (CA);
Hassan Pajouhesh, Vancouver (CA);
Hossein Pajouhesh, Burnaby (CA);
Francesco Belardetti, Vancouver (CA)

(73) Assignee: NeuroMED Technologies Inc., Vancouver (CA)

( * ) Notice: Subject to any disclaimer, the term of this patent is extended or adjusted under 35 U.S.C. 154(b) by 0 days.

(21) Appl. No.: 10/409,868

(22) Filed: Apr. 8, 2003

(65) Prior Publication Data

US 2004/0044004 A1 Mar. 4, 2004

Related U.S. Application Data

(63) Continuation-in-part of application No. 10/060,900, filed on Jan. 29, 2002, now Pat. No. 6,617,322, which is a continuation of application No. 09/476,927, filed on Dec. 30, 1999, now Pat. No. 6,387,897, which is a continuation-in-part of application No. 09/401,699, filed on Sep. 23, 1999, now Pat. No. 6,294,533, which is a continuation-in-part of application No. 09/107,037, filed on Jun. 30, 1998, now Pat. No. 6,011,035.

(51) Int. Cl.$^7$ .................. A61K 31/497; A61K 31/4965; C07D 401/00; C07D 295/00
(52) U.S. Cl. ......................... 514/252.13; 514/254.02; 514/255.01; 544/361; 544/362; 544/386
(58) Field of Search ................... 514/252.13, 254.02, 514/255.01; 544/361, 362, 386

(56) References Cited

U.S. PATENT DOCUMENTS

| | | | |
|---|---|---|---|
| 3,288,795 A | 11/1966 | Irikura et al. | |
| 4,188,485 A | 2/1980 | Kukla | |
| 4,918,073 A | 4/1990 | Ruger et al. | |
| 5,386,025 A | 1/1995 | Jay et al. | 536/23.5 |
| 5,428,038 A | 6/1995 | Chatterjee et al. | 514/253 |
| 5,623,051 A | 4/1997 | Catterall et al. | 530/324 |
| 5,646,149 A | 7/1997 | Hellberg et al. | 514/253 |
| 5,703,071 A | 12/1997 | Itoh et al. | 514/218 |
| 5,866,574 A * | 2/1999 | Okamura et al. | 514/245 |
| 6,011,035 A | 1/2000 | Snutch et al. | 514/231.2 |
| 6,294,533 B1 | 9/2001 | Snutch et al. | 514/231.2 |
| 6,310,059 B1 | 10/2001 | Snutch | 514/222.2 |
| 6,387,897 B1 | 5/2002 | Snutch | 514/231.2 |
| 6,458,781 B1 * | 10/2002 | Connor et al. | 514/212.03 |
| 2001/0029258 A1 | 10/2001 | Snutch | 514/231.2 |
| 2004/0034035 A1 | 2/2004 | Pajouhesh et al. | 514/255.01 |

FOREIGN PATENT DOCUMENTS

| | | |
|---|---|---|
| CA | 2335461 | 6/1999 |
| CA | 2394327 | 6/2001 |
| EP | 0 187 524 | 7/1986 |
| EP | 0 213006 A | 3/1987 |
| EP | 0 458387 | 11/1991 |
| EP | 0 496 691 | 7/1992 |
| ES | 504 202 | 1/1983 |
| ES | 514 167 | 4/1983 |
| ES | 8 304 135 | 5/1983 |
| ES | 8 305 343 | 7/1983 |
| GB | 920 416 | 3/1963 |
| GB | 1 513 883 | 6/1978 |
| WO | WO 94/14786 A | 7/1994 |
| WO | WO 99/15129 | 4/1999 |
| WO | WO 99/25686 | 5/1999 |
| WO | WO 00/01375 A | 1/2000 |
| WO | WO 00/18402 A | 4/2000 |
| WO | WO 00/37059 A | 6/2000 |
| WO | WO 01/45709 | 6/2001 |
| WO | WO-01/49670 | 7/2001 |
| WO | WO-03/068759 | 8/2003 |

OTHER PUBLICATIONS

Bourinet et al., "Splicing of $\alpha_{1A}$ Subunit Gene Generates Phenotypic Variants of P– and Q–Type Calcium Channels," Nature Neuroscience (1999) 2:407–415.

Chiarini, A. et al., "1,4–Dihydropyridines Bearing a Pharmacophoric Fragment of Lidoflazine" Bioorg & Med Chemistry (1996) 4(10):1629–1635.

Cohan, S. et al., Annals of the New York Academy of Sciences (1991) 635:397–399.

Cribbs et al., "Cloning and Characterization of $\alpha 1H$ from Human Heart, A Member of the T–Type $Ca^{2+}$ Channel Gene Family," Circulation Research (1998) 83:103–109.

Database WPI Week 9711 Derwent Publications Ltd., London, GB; Abstract JP 09 003067, XP002133055 (Hisamitsu Pharm Co Ltd.) Jan. 7, 1997.

De Waard et al., "Structural and Functional Diversity of Voltage–Activated Calcium Channels," ION Channels (Narahashi, T. ed. Plenum Press, NY (1997) 4:41–87.

Dhainaut et al., J of Medicinal Chemistry (1992) 35:2481–2496.

Dooley, "Lomerizine Kanebo KK" Current Opinion In CPNS Investigational Drugs (1999) 1(1):116–125.

Dunlap et al., "Exocytotic $Ca^{2+}$ Channels in Mammalian Central Neurons," Trends Neurosci (1995) 18:89–98.

Estep, K. et al., J of Medicinal Chemistry (1995) 38(14):2582–2595.

Galizzi et al., "Neuroleptics of the Diphenylbutylpiperidine Series are Potent Calcium Channel Inhibitors," Proc Natl Acad Sci USA (1986) 83: 7513–7517.

Glamkowski, E. et al., J of Medicinal Chemistry (1977) 20(11):1485–1489.

Gould et al., " Antischizophrenic Drugs of the Diphenylbutylpiperidine Type Act as Calcium Channel Antagonists," Proc Natl Acad Sci (1983) 80:5122–5125.

(Continued)

Primary Examiner—Raymond J. Henley, III
(74) Attorney, Agent, or Firm—Morrison & Foerster LLP

(57) ABSTRACT

Certain piperazine substituted compounds are described which are useful in altering calcium channel activity.

29 Claims, 15 Drawing Sheets

OTHER PUBLICATIONS

Grantham et al., "Fluspirilene Block of N–Type Calcium Current in NGF–Differentiated PC12 Cells," Brit J Pharmacol (1994) 111:438–488.

Ito et al., "U–92032, a T–Type $Ca^{2+}$ Channel Blocker and Antioxidant, Reduces Neuronal Ischemic Injuries," Eur J Pharmacol (1994) 257:203–210.

King et al., "Substituted Diphenylbutylpiperidines Bind to a Unique High Affinity Site on the L–Type Calcium Channel," J Biol Chem (1989) 264:5633–5641.

Lee et al., "Cloning and Expression of a Novel Member of the Low Voltage–Activated T–Type Calcium Channel Family," Journal of Neuroscience (1999) 19:1912–1921.

Lehmann et al., Archiv der Pharmazie (1988) 321(11):807–812.

McCleskey et al., "Functional Properties of Voltage Dependent Calcium Channels," Curr Topics Membr (1991) 39:295–326.

Miyano, S. et al., Chem Pharm Bull (1990) 38(6):1570–1574.

Ohtaka, H. et al., Chem Pharm Bull (1987) 35(10):4117–4123.

Ohtaka, H. et al., Chem Pharm Bull (1987) 35(8):3270–3275.

Perez–Reyes et al., "Molecular Characterization of a Neuronal Low–Voltage–Activated T–Type Calcium Channel," Nature (1998) 391:896–900.

Prasad, R. et al., J of Medicinal Chemistry (1968) 11(6):1144–1150.

Sather et al., "Distinctive Biophysical and Pharmacological Properties of Class A (BI) Calcium Channel $\alpha_1$ Subunits," Neuron (1993) 11:291–303.

Stea et al., "Localization and Functional Properties of a Rat Brain $\alpha_{1A}$ Calcium Channel Reflect Similarities to Neuronal Q– and P–Type Channels," Proc Natl Acad Sci USA (1994) 91:10576–10580.

Stea et al., Handbook of Receptors and Channels (North, R.A. ed. CRC Press (1995) 113–151.

Tytgat, J. et al., Brain Research (1991) 549(1):112–117.

Uneyama, H. et al., Calcium Ion Modulators, Sel Pap Satell Symp (1998) 13–23.

Vadodaria, D. et al., J of Medicinal Chemistry (1969) 12:860–865.

Zikolova, S. et al., Tr. Nauchnoizsled Khim–Farm Inst (1972) 8:59–67.

Zikolova, S. et al., Tr. Nauchnoizsled Khim–Farm Inst (1984) 14:23–28.

International Search Report for PCT/CA2004/000535, mailed on Jul. 1, 2004, 5 pages.

Invitation to Pay Additional Fees for PCT/CA2004/000539, mailed on Sep. 2, 2004, 6 pages.

Boger et al., Helvetica Chimica Acta (2000) 83(8): 1825–1845.

International Search Report for PCT/CA2004/000539, mailed on Dec. 22, 2004, 9 pages.

International Search Report for PCT/CA2004/001629, mailed on Jan. 21, 2005, 6 pages.

Jamieson et al., Synlett (2000) 11:1603–1607.

Toldy et al., Acta Chimica Academiae Scientiarum Hungarica (1965) 44:301–325.

Webster et al., Journal of the Chemical Society (2001) 14:1673–1695.

\* cited by examiner

| Compound | Name | Structure |
|---|---|---|
| P1 | 6,6-Bis-(4-fluoro-phenyl)-1-[4-(2-phenylsulfanyl-ethyl)-piperazin-1-yl]-hexan-1-one | 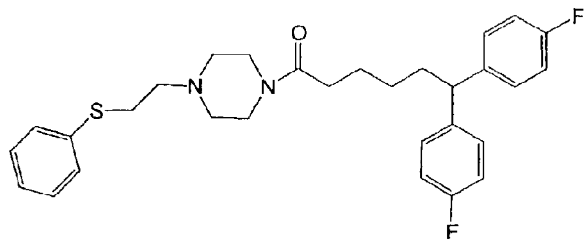 |
| P2 | 1-[6,6-Bis-(4-fluoro-phenyl)-hexyl]-4-[2-(4-fluoro-phenoxy)-ethyl]-piperazine | 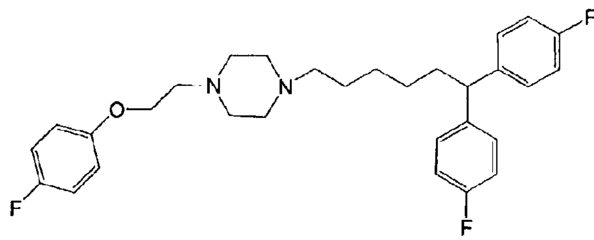 |
| P3 | 1-{4-[2-(Benzo[1,3]dioxol-5-yloxy)-ethyl]-piperazin-1-yl}-6,6-bis-(4-fluoro-phenyl)-hexan-1-one |  H—Cl |
| P4 | 1-[6,6-Bis-(4-fluoro-phenyl)-hexyl]-4-(2-phenylsulfanyl-ethyl)-piperazine | 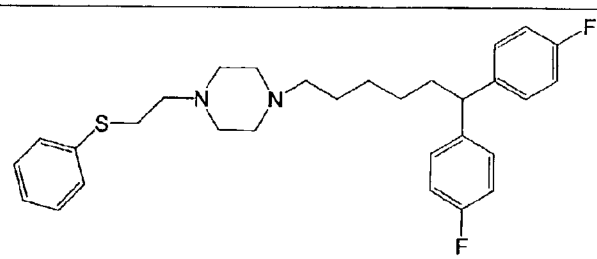 |
| P5 | 1-[6,6-Bis-(4-fluoro-phenyl)-hexyl]-4-[2-(4-methoxy-phenoxy)-ethyl]-piperazine |  H—Cl H—Cl |

Page 1 of 13

| Compound | Name | Structure |
|---|---|---|
| P6 | 1-{4-[2-(2,4-Difluoro-phenoxy)-ethyl]-piperazin-1-yl}-6,6-bis-(4-fluoro-phenyl)-hexan-1-one | 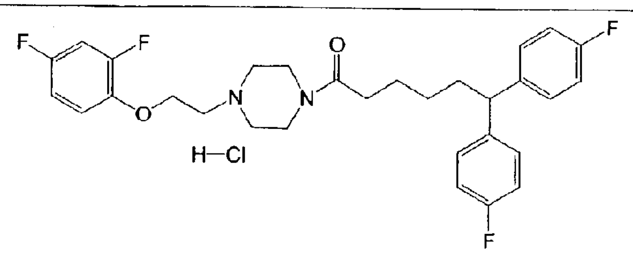 |
| P7 | 6,6-Bis-(4-fluoro-phenyl)-1-[4-(2-phenoxy-ethyl)-piperazin-1-yl]-hexan-1-one | 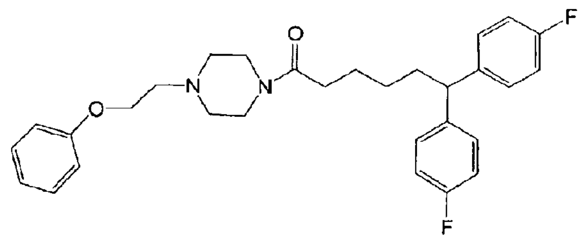 |
| P8 | 1-{4-[2-(2,4-Dichloro-phenoxy)-ethyl]-piperazin-1-yl}-6,6-bis-(4-fluoro-phenyl)-hexan-1-one | 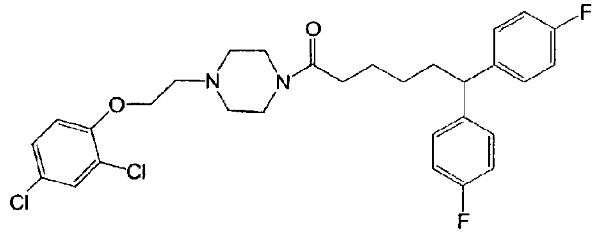 |
| P9 | 6,6-Bis-(4-fluoro-phenyl)-1-{4-[2-(4-methoxy-phenoxy)-ethyl]-piperazin-1-yl}-hexan-1-one | 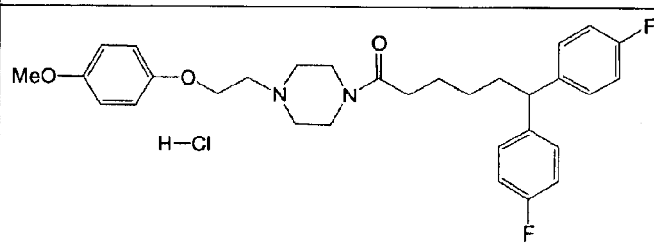 |
| P10 | 1-[6,6-Bis-(4-fluoro-phenyl)-hexyl]-4-(2-phenoxy-ethyl)-piperazine | 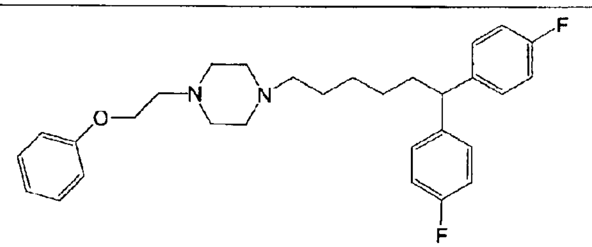 |

Figure 1

Page 2 of 13

| Compound | Name | Structure |
|---|---|---|
| P11 | 6,6-Bis-(4-fluoro-phenyl)-1-{4-[2-(3,4,5-trimethoxy-phenoxy)-ethyl]-piperazin-1-yl}-hexan-1-one | 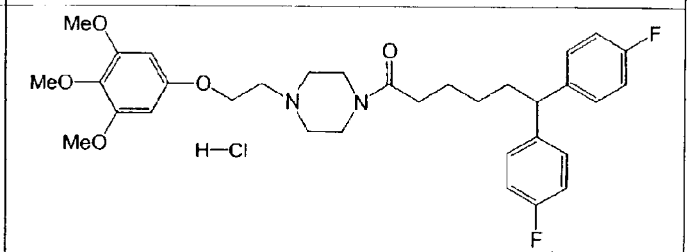 |
| P12 | 1-{4-[2-(Benzothiazol-2-ylsulfanyl)-ethyl]-piperazin-1-yl}-6,6-bis-(4-fluoro-phenyl)-hexan-1-one | 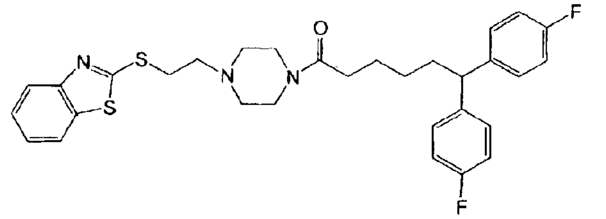 |
| P13 | [4-(2-{4-[6,6-Bis-(4-fluoro-phenyl)-hexanoyl]-piperazin-1-yl}-ethoxy)-2,3,6-trimethyl-phenyl]-carbamic acid tert-butyl ester | 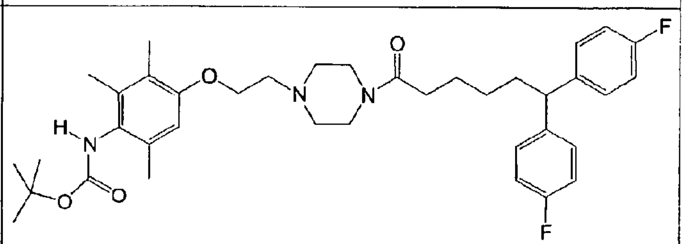 |
| P14 | 4-(2-{4-[6,6-Bis-(4-fluoro-phenyl)-hexyl]-piperazin-1-yl}-ethoxy)-2,3,6-trimethyl-phenylamine | 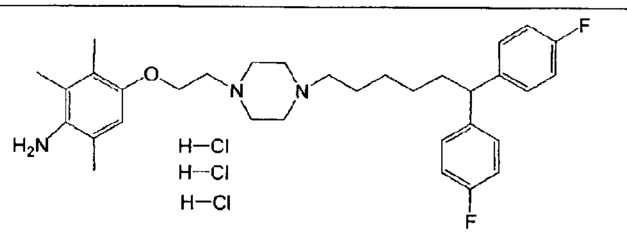 |
| P15 | 1-[6,6-Bis-(4-fluoro-phenyl)-hexyl]-4-[2-(2,4-dichloro-phenoxy)-ethyl]-piperazine | 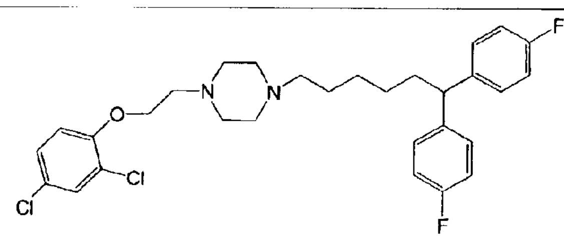 |

Figure 1

Page 3 of 13

| Compound | Name | Structure |
|---|---|---|
| P16 | [2-(4-{4-[6,6-Bis-(4-fluoro-phenyl)-hexyl]-piperazin-1-ylmethyl}-2,6-di-tert-butyl-phenoxy)-ethyl]-dimethyl-amine | 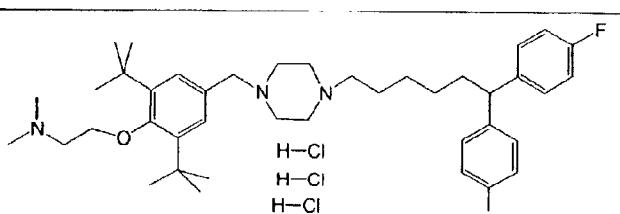 |
| P17 | 4-{4-[6,6-Bis-(4-fluoro-phenyl)-hexyl]-piperazin-1-ylmethyl}-2,6-di-tert-butyl-phenol | 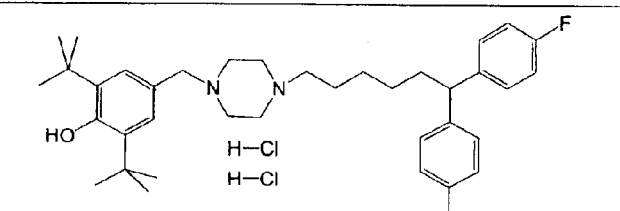 |
| P18 | 1-[4-(3,5-Di-tert-butyl-4-methoxy-benzoyl)-piperazin-1-yl]-6,6-bis-(4-fluoro-phenyl)-hexan-1-one | 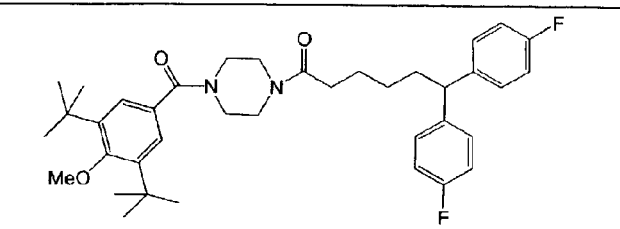 |
| P19 | 1-[4-(3,5-Di-tert-butyl-4-methoxy-benzyl)-piperazin-1-yl]-6,6-bis-(4-fluoro-phenyl)-hexan-1-one | 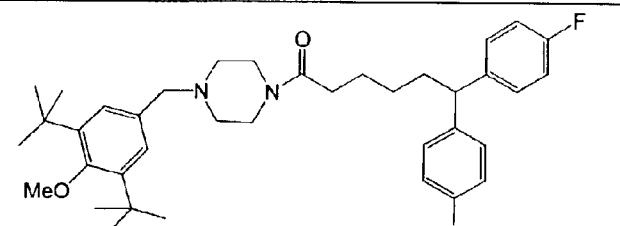 |
| P20 | 1-[6,6-Bis-(4-fluoro-phenyl)-hexyl]-4-(3,5-di-tert-butyl-4-methoxy-benzyl)-piperazine | 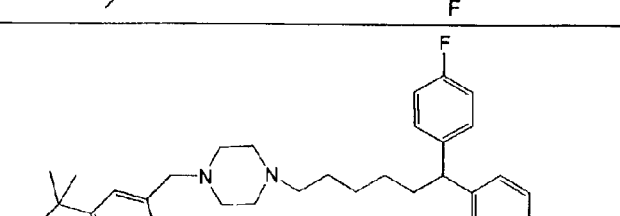 |

Figure 1

Page 4 of 13

| Compound | Name | Structure |
|---|---|---|
| P21 | {4-[6,6-Bis-(4-fluoro-phenyl)-hexyl]-piperazin-1-yl}-(3,5-di-tert-butyl-4-methoxy-phenyl)-methanone | 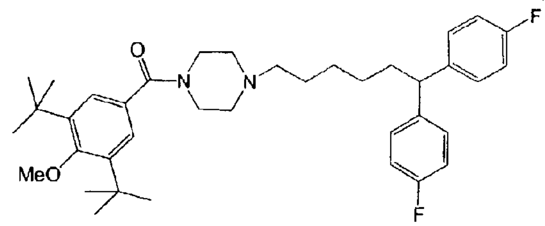 |
| P22 | 1-{4-[3,5-Di-tert-butyl-4-(2-dimethylamino-ethoxy)-benzoyl]-piperazin-1-yl}-6,6-bis-(4-fluoro-phenyl)-hexan-1-one | 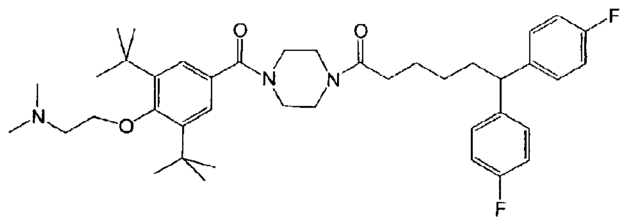 |
| P23 | 1-Benzo[1,3]dioxol-5-ylmethyl-4-[6,6-bis-(4-fluoro-phenyl)-hexyl]-piperazine | 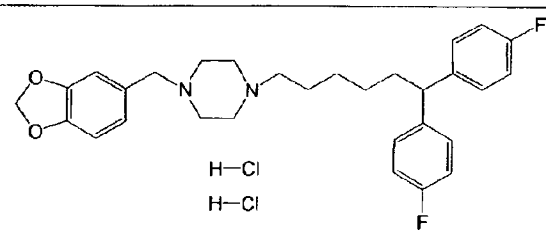 |
| P24 | 1-[6,6-Bis-(4-fluoro-phenyl)-hexyl]-4-(3,5-di-tert-butyl-benzyl)-piperazine | 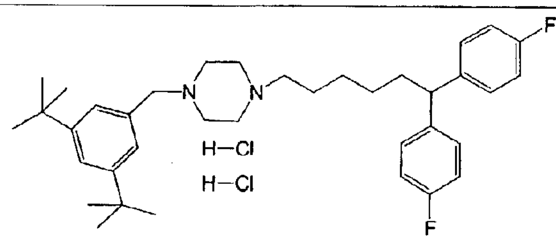 |
| P25 | {4-[6,6-Bis-(4-fluoro-phenyl)-hexyl]-piperazin-1-yl}-(3,5-di-tert-butyl-4-hydroxy-phenyl)-methanone | 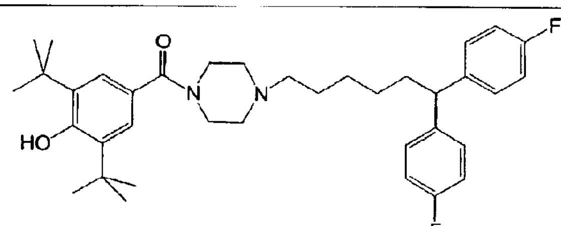 |

Figure 1

Page 5 of 13

| Compound | Name | Structure |
|---|---|---|
| P26 | 1-[4-(3,5-Di-tert-butyl-4-hydroxy-benzyl)-piperazin-1-yl]-6,6-bis-(4-fluoro-phenyl)-hexan-1-one | 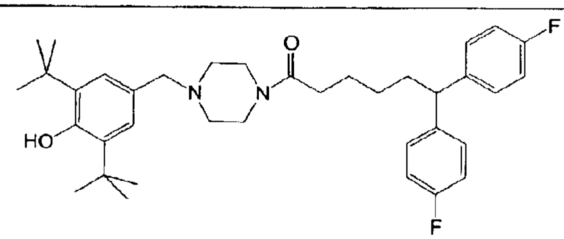 |
| P27 | 1-[4-(3,5-Dibromo-4-hydroxy-benzoyl)-piperazin-1-yl]-6,6-bis-(4-fluoro-phenyl)-hexan-1-one | 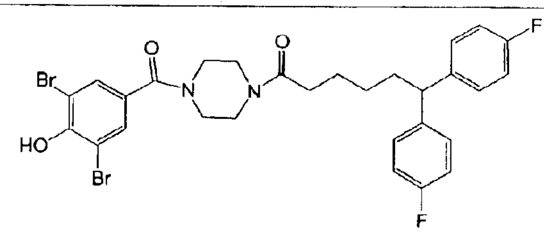 |
| P28 | 1-[4-(3,5-Di-tert-butyl-4-hydroxy-benzoyl)-piperazin-1-yl]-6,6-bis-(4-fluoro-phenyl)-hexan-1-one | 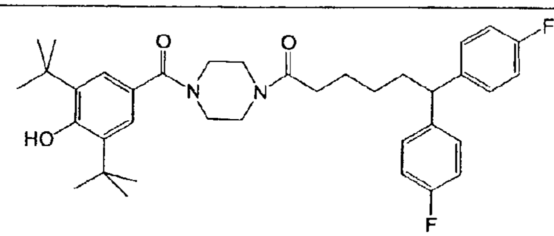 |
| P29 | 1-[4-(3,5-Di-tert-butyl-benzoyl)-piperazin-1-yl]-6,6-bis-(4-fluoro-phenyl)-hexan-1-one | 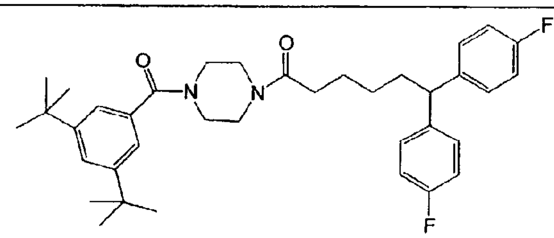 |
| P30 | 1-[6,6-Bis-(4-fluoro-phenyl)-hexyl]-4-(4-tert-butyl-benzyl)-piperazine | 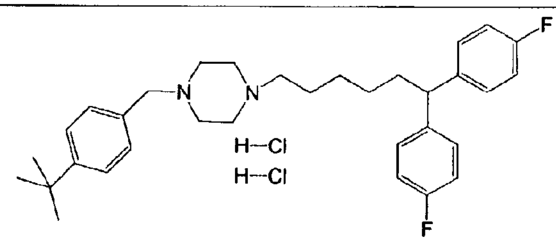 |

Figure 1

Page 6 of 13

| Compound | Name | Structure |
|---|---|---|
| P31 | 1-[6,6-Bis-(4-fluoro-phenyl)-hexyl]-4-(9H-thioxanthen-9-yl)-piperazine | 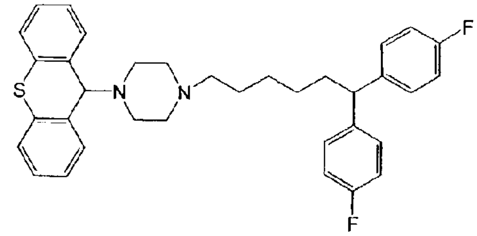 |
| P32 | 2-{4-[6,6-Bis-(4-fluoro-phenyl)-hexyl]-piperazin-1-yl}-benzothiazole | 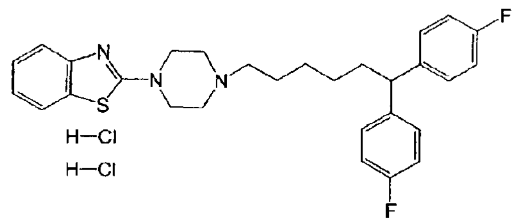 |
| P33 | 6,6-Bis-(4-fluoro-phenyl)-1-(4-pyrimidin-2-yl-piperazin-1-yl)-hexan-1-one | 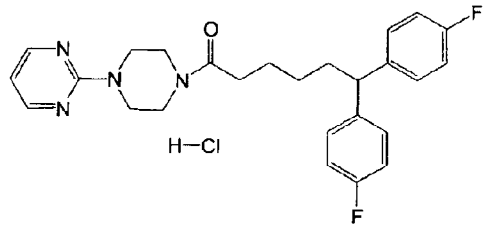 |
| P34 | 2-{4-[6,6-Bis-(4-fluoro-phenyl)-hexyl]-piperazin-1-yl}-pyrimidine | 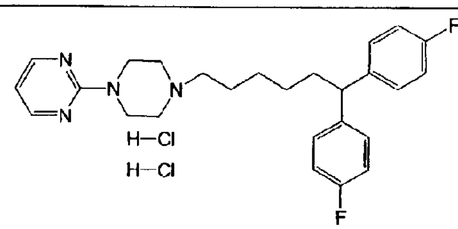 |
| P35 | 6,6-Bis-(4-fluoro-phenyl)-1-[4-(9H-thioxanthen-9-yl)-piperazin-1-yl]-hexan-1-one | 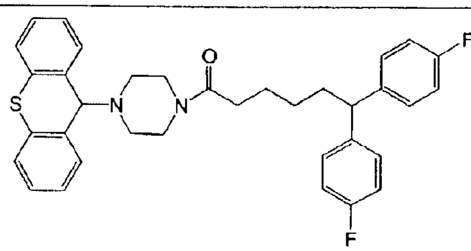 |

Figure 1

Page 7 of 13

| Compound | Name | Structure |
|---|---|---|
| P36 | 1-[6,6-Bis-(4-fluoro-phenyl)-hexyl]-4-(3,4,5-trimethoxy-benzyl)-piperazine-2-carboxylic acid ethyl ester | 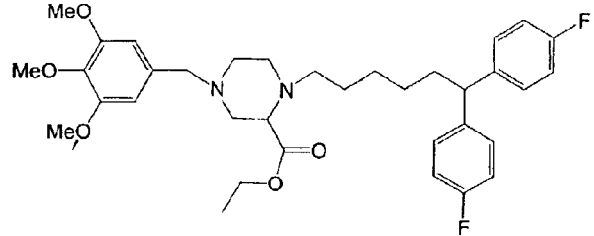 |
| P37 | 6,6-Bis-(4-fluoro-phenyl)-1-{4-[2-(3,4,5-trimethoxy-benzylamino)-ethyl]-piperazin-1-yl}-hexan-1-one | 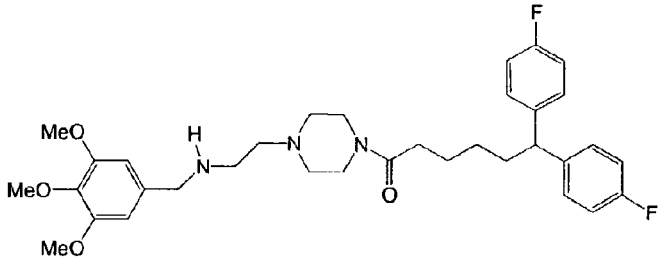 |
| P38 | 9,9-Bis-(4-fluoro-phenyl)-1-[4-(3,4,5-trimethoxy-benzyl)-piperazin-1-yl]-nonan-1-one | 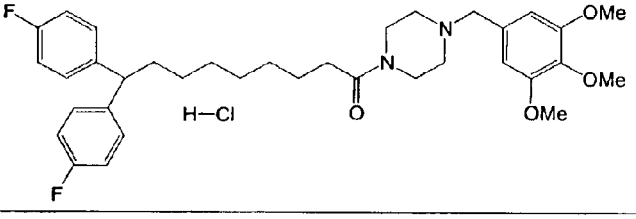 |
| P39 | (2-{4-[6,6-Bis-(4-fluoro-phenyl)-hexyl]-piperazin-1-yl}-ethyl)-phenyl-amine | 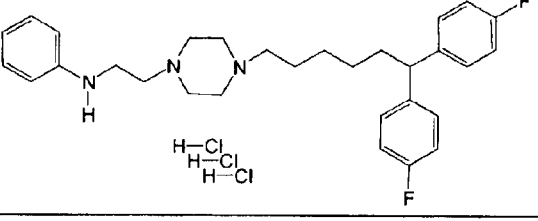 |
| P40 | 1-[9,9-Bis-(4-fluoro-phenyl)-nonyl]-4-(3,4,5-trimethoxy-benzyl)-piperazine | 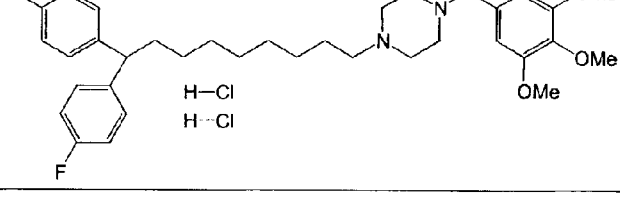 |

Figure 1

Page 8 of 13

| Compound | Name | Structure |
|---|---|---|
| P41 | (4-{4-[Bis-(4-fluoro-phenyl)-methoxy]-butyl}-piperazin-1-yl)-(3,4,5-trimethoxy-phenyl)-methanone | 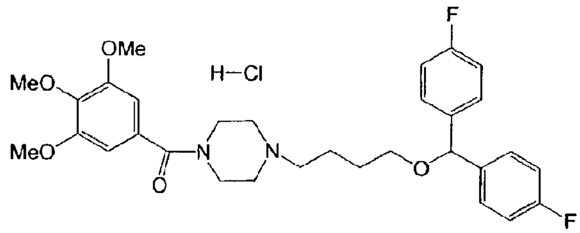 |
| P42 | 6,6-Bis-(4-fluoro-phenyl)-1-[4-(4-trifluoromethoxy-benzoyl)-piperazin-1-yl]-hexan-2-one | 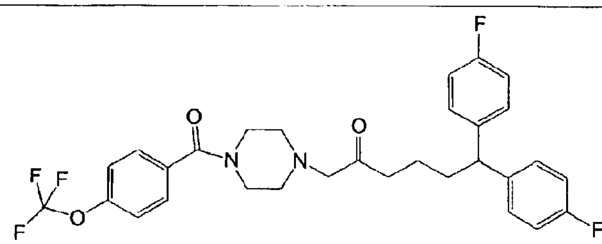 |
| P43 | 1-[4-(4-Bromo-benzoyl)-piperazin-1-yl]-6,6-bis-(4-fluoro-phenyl)-hexan-1-one | 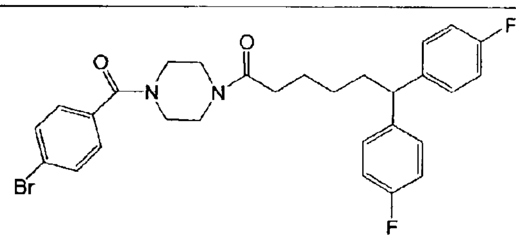 |
| P44 | 6,6-Bis-(4-fluoro-phenyl)-5-hydroxy-1-[4-(3,4,5-trimethoxy-benzoyl)-piperazin-1-yl]-hexan-1-one | 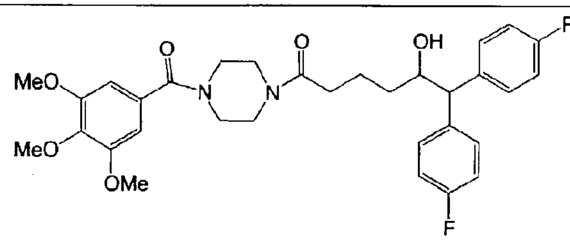 |
| P45 | 1-{4-[Bis-(4-fluoro-phenyl)-methoxy]-butyl}-4-(3,4,5-trimethoxy-benzyl)-piperazine | 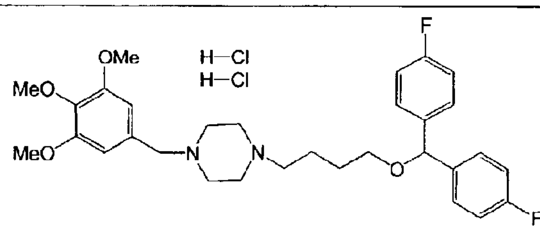 |

Figure 1

Page 9 of 13

| Compound | Name | Structure |
|---|---|---|
| P46 | 6,6-Bis-(4-fluoro-phenyl)-6-hydroxy-1-[4-(3,4,5-trimethoxy-benzoyl)-piperazin-1-yl]-hexan-1-one | 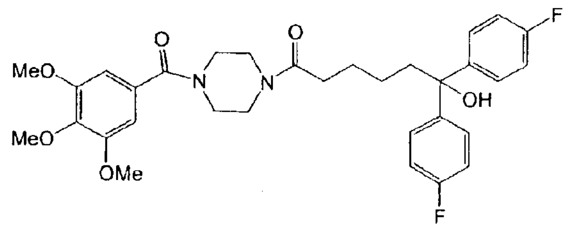 |
| P47 | 4-[6,6-Bis-(4-fluoro-phenyl)-hexyl]-1-(3,4,5-trimethoxy-benzyl)-piperazine-2-carboxylic acid | 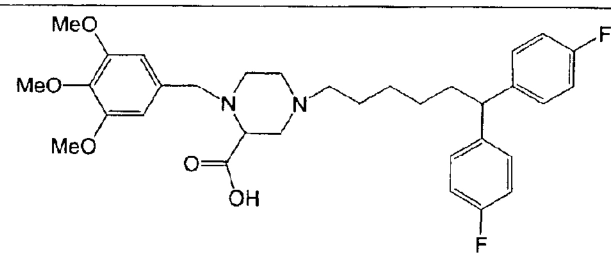 |
| P48 | 4-[6,6-Bis-(4-fluoro-phenyl)-hexanoyl]-1-(3,4,5-trimethoxy-benzyl)-piperazin-2-one | 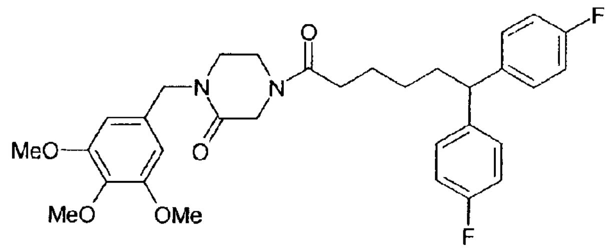 |
| P49 | 1-[6,6-Bis-(4-fluoro-phenyl)-hexanoyl]-4-(3,5-di-tert-butyl-4-methoxy-benzoyl)-piperazin-2-one | 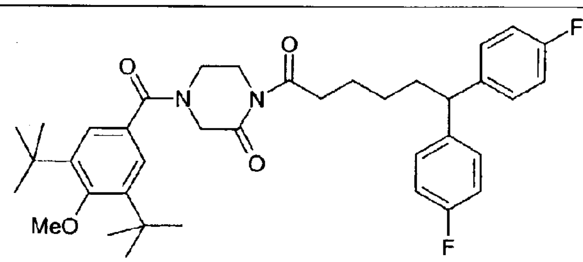 |
| P50 | 1-[6,6-Bis-(4-fluoro-phenyl)-hexyl]-4-(3,4,5-trimethoxy-benzoyl)-piperazin-2-one | 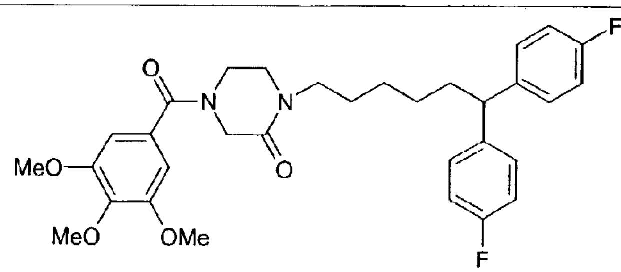 |

Figure 1

Page 10 of 13

| Compound | Name | Structure |
|---|---|---|
| P51 | 4-[6,6-Bis-(4-fluoro-phenyl)-hexyl]-1-(3,4,5-trimethoxy-benzyl)-piperazin-2-one | 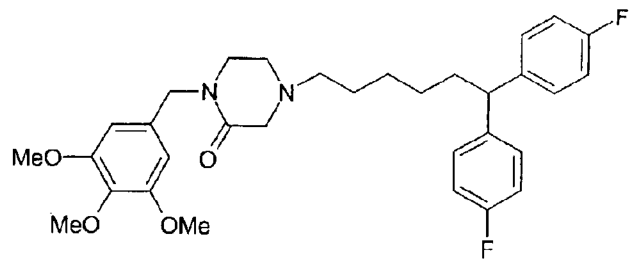 |
| P52 | 4-[6,6-Bis-(4-fluoro-phenyl)-hexanoyl]-1-(3,5-di-tert-butyl-4-methoxy-benzyl)-piperazin-2-one | 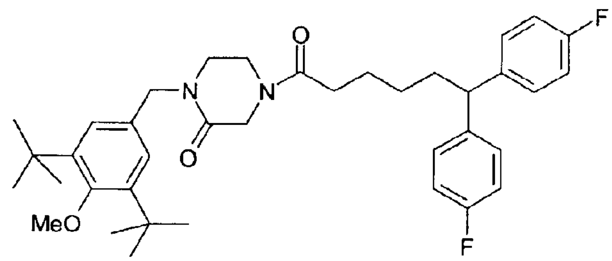 |
| P53 | 4-[6,6-Bis-(4-fluoro-phenyl)-hexanoyl]-1-[2-(4-fluoro-phenoxy)-ethyl]-piperazin-2-one | 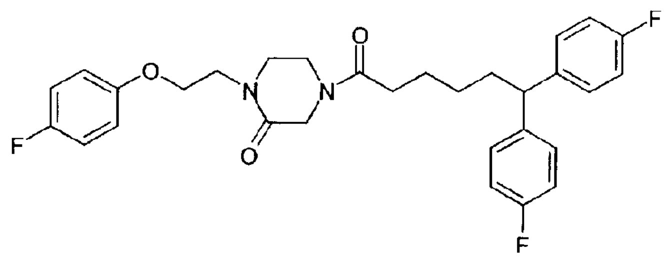 |
| P54 | 1-[6,6-Bis-(4-fluoro-phenyl)-hexyl]-4-(3,5-di-tert-butyl-4-methoxy-benzoyl)-piperazin-2-one | 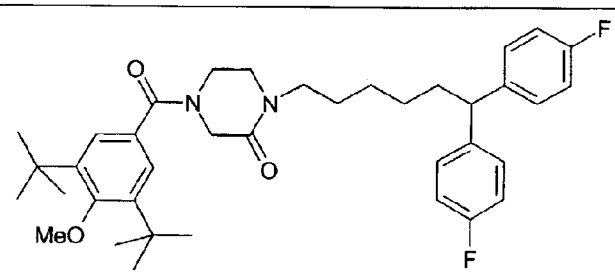 |

Figure 1

| Compound | Name | Structure |
|---|---|---|
| P55 | 4-[6,6-Bis-(4-fluoro-phenyl)-hexanoyl]-1-(3,5-di-tert-butyl-4-methoxy-benzoyl)-piperazin-2-one | 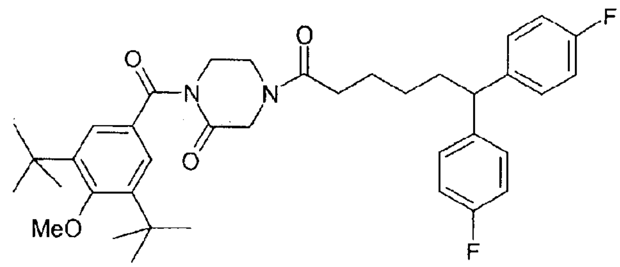 |
| P56 | 1-[6,6-Bis-(4-fluoro-phenyl)-hexyl]-4-(3,5-di-tert-butyl-4-methoxy-benzyl)-piperazin-2-one | 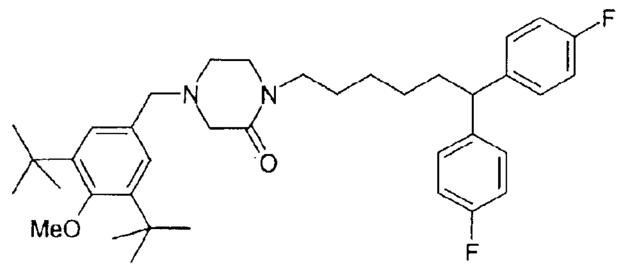 |
| P57 | 1-[6,6-Bis-(4-fluoro-phenyl)-hexanoyl]-4-(3,5-di-tert-butyl-4-hydroxy-benzoyl)-piperazin-2-one | 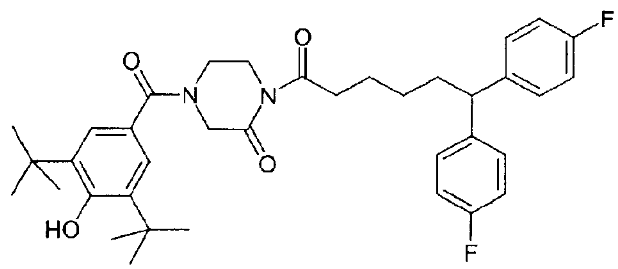 |
| P58 | 6,6-Bis-(4-fluoro-phenyl)-1-[4-(3,4,5-trimethoxy-benzoyl)-piperazin-1-yl]-hex-5-en-1-one | 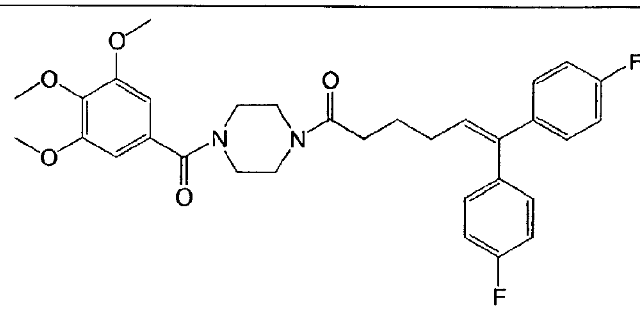 |

Figure 1

| Compound | Name | Structure |
|---|---|---|
| P59 | 1-{4-[2-(3,4-Dimethoxy-phenoxy)-ethyl]-piperazin-1-yl}-6,6-bis-(4-fluoro-phenyl)-hexan-1-one | 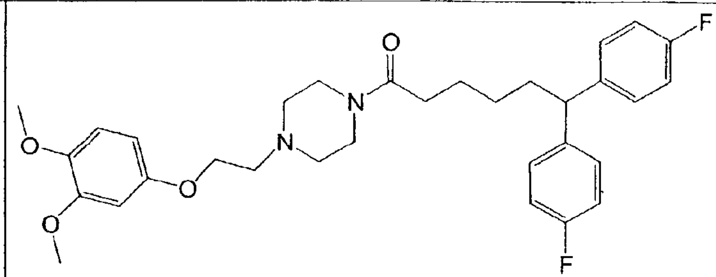 |
| P60 | 1-[6,6-Bis-(4-fluoro-phenyl)-hexyl]-4-[2-(3,4-dimethoxy-phenoxy)-ethyl]-piperazine | 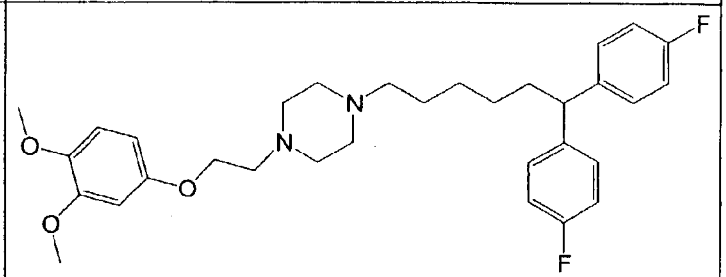 |

CALCIUM CHANNEL INHIBITORS COMPRISING BENZHYDRIL SPACED FROM PIPERAZINE

CROSS-REFERENCE TO RELATED APPLICATIONS

This application is a continuation-in-part of U.S. Ser. No. 10/060,900 filed 29 Jan. 2002, now U.S. Pat. No. 6,617,322; which is a continuation of U.S. Ser. No. 09/476,927 filed 30 Dec. 1999, now U.S. Pat. No. 6,387,897; which is a continuation-in-part of U.S. Ser. No. 09/401,699, filed 23 Sep. 1999, now U.S. Pat. No. 6,294,533; which is a continuation-in-part of U.S. Ser. No. 09/107,037 filed 30 Jun. 1998, now U.S. Pat. No. 6,011,035. The contents of these applications are incorporated herein by reference.

TECHNICAL FIELD

The invention relates to compounds useful in treating conditions associated with abnormal calcium channel function. More specifically, the invention concerns compounds containing substituted or unsubstituted derivatives of 6-membered heterocyclic moieties that are useful in treatment of conditions such as stroke and pain.

BACKGROUND ART

PCT publication WO 01/45709 published 28 Jun. 2001 discloses calcium channel blockers where a piperidine or piperazine ring links a benzhydril moiety to an additional aromatic moiety or benzhydril. This publication, which is based on parent application Ser. No. 09/476,927, discussed above, is incorporated herein by reference. As explained in these applications, native calcium channels have been classified by their electrophysiological and pharmacological properties as T, L, N, P and Q types. T-type (or low voltage-activated) channels describe a broad class of molecules that transiently activate at negative potentials and are highly sensitive to changes in resting potential. The L, N, P and Q-type channels activate at more positive potentials (high voltage activated) and display diverse kinetics and voltage-dependent properties. There is some overlap in biophysical properties of the high voltage-activated channels, consequently pharmacological profiles are useful to further distinguish them. Whether the Q- and P-type channels are distinct molecular entities is controversial. Several types of calcium conductances do not fall neatly into any of the above categories and there is variability of properties even within a category suggesting that additional calcium channels subtypes remain to be classified.

Biochemical analyses show that neuronal high voltage activated calcium channels are heterooligomeric complexes consisting of at least three distinct subunits ($\alpha_1$, $\alpha_2\delta$ and $\beta$). The $\alpha_1$ subunit is the major pore-forming subunit and contains the voltage sensor and binding sites for calcium channel antagonists. The mainly extracellular $\alpha_2$ is disulfide-linked to the transmembrane $\delta$ subunit and both are derived from the same gene and are proteolytically cleaved in vivo. The $\beta$ subunit is a nonglycosylated, hydrophilic protein with a high affinity of binding to a cytoplasmic region of the $\alpha_1$ subunit. A fourth subunit, $\gamma$, is unique to L-type calcium channels expressed in skeletal muscle T-tubules.

Recently, each of these $\alpha_1$ subtypes has been cloned and expressed, thus permitting more extensive pharmacological studies. These channels have been designated $\alpha_{1A}$–$\alpha_{1I}$ and $\alpha_{1S}$ and correlated with the subtypes set forth above. $\alpha_{1A}$ channels are of the P/Q type; $\alpha_{1B}$ represents N; $\alpha_{1C}$, $\alpha'_{1D}$, $\alpha_{1F}$ and $\alpha_{1S}$ represent L; $\alpha_{1E}$ represents a novel type of calcium conductance, and $\alpha_{1G}$–$\alpha_{1I}$ represent members of the T-type family.

Further details concerning the function of N-type channels, which are mainly localized to neurons, have been disclosed, for example, in U.S. Pat. No. 5,623,051, the disclosure of which is incorporated herein by reference. As described, N-type channels possess a site for binding syntaxin, a protein anchored in the presynaptic membrane. Blocking this interaction also blocks the presynaptic response to calcium influx. Thus, compounds that block the interaction between syntaxin and this binding site would be useful in neural protection and analgesia. Such compounds have the added advantage of enhanced specificity for presynaptic calcium channel effects.

U.S. Pat. No. 5,646,149 describes calcium channel antagonists of the formula A—Y—B wherein B contains a piperazine or piperidine ring directly linked to Y. An essential component of these molecules is represented by A, which must be an antioxidant; the piperazine or piperidine itself is said to be important. The exemplified compounds contain a benzhydril substituent, based on known calcium channel blockers (see below). In some cases, the antioxidant can be a phenyl group containing methoxy and/or hydroxyl substituents. In most of the illustrative compounds, however, a benzhydril moiety is coupled to the heterocycle simply through a CH group or C= group. In the few compounds where there is an alkylene chain between the CH to which the two phenyl groups are bound and the heterocycle, the antioxidant must be coupled to the heterocycle through an unsubstituted alkylene and in most of these cases the antioxidant is a bicyclic system. Where the antioxidant can simply be a phenyl moiety coupled through an alkynylene, the linker from the heterocycle to the phenyl moieties contains no more than six atoms in the chain. U.S. Pat. No. 5,703,071 discloses compounds said to be useful in treating ischemic diseases. A mandatory portion of the molecule is a tropolone residue; among the substituents permitted are piperazine derivatives, including their benzhydril derivatives. U.S. Pat. No. 5,428,038 discloses compounds which are said to exert a neural protective and antiallergic effect. These compounds are coumarin derivatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to maintain functionality.

Certain compounds containing both benzhydril moieties and piperidine or piperazine are known to be calcium channel antagonists and neuroleptic drugs. For example, Gould, R. J., et al., *Proc. Natl. Acad. Sci. USA* (1983) 80:5122–5125 describes antischizophrenic neuroleptic drugs such as lidoflazine, fluspirilene, pimozide, clopimozide, and penfluridol. It has also been shown that fluspirilene binds to sites on L-type calcium channels (King, V. K., et al., *J. Biol. Chem.* (1989) 264:5633–5641) as well as blocking N-type calcium current (Grantham, C. J., et al., *Brit. J. Pharmacol.* (1944) 111:483–488). In addition, Lomerizine, as developed by Kanebo, K. K., is a known calcium channel blocker; Lomerizine is, however, not specific for N-type channels. A review of publications concerning Lomerizine is found in Dooley, D., *Current Opinion in CPNS Investigational Drugs* (1999) 1:116–125.

In addition, benzhydril derivatives of piperidine and piperazine are described in PCT publication WO 00/01375 published 13 Jan. 2000 and incorporated herein by reference. This PCT publication corresponds to grandparent application Ser. No. 09/401,699 set forth above. Reference to this type of compound as known in the prior art is also made in WO 00/18402 published 6 Apr. 2000 and in Chiarini, A., et al., *Bioorganic and Medicinal Chemistry*, (1996) 4:1629–1635.

Various other piperidine or piperazine derivatives containing aryl substituents linked through nonaromatic linkers are described as calcium channel blockers in U.S. Pat. No. 5,292,726; WO 99/43658; Breitenbucher, J. G., et al., *Tat Lett* (1998) 39:1295–1298.

The present invention is based on the recognition that the combination of a six-membered heterocyclic ring containing at least one nitrogen said nitrogen coupled through a linker to a benzhydril moiety results in effective calcium channel blocking activity. In some cases enhanced specificity for N-type channels and/or T-type channels, or decreased specificity for L-type channels is shown. The compounds are useful for treating stroke and pain and other calcium channel-associated disorders, as further described below. By focusing on these moieties, compounds useful in treating indications associated with calcium channel activity are prepared.

DISCLOSURE OF THE INVENTION

The invention relates to compounds useful in treating conditions such as stroke, anxiety, overactive bladder, inflammatory bowel disease, head trauma, migraine, chronic, neuropathic and acute pain, epilepsy, hypertension, cardiac arrhythmias, and other indications associated with calcium metabolism, including synaptic calcium channel-mediated functions. The compounds of the invention are benzhydril derivatives of piperazine with substituents that enhance the calcium channel blocking activity of the compounds. Thus, in one aspect, the invention is directed to compounds of the formula

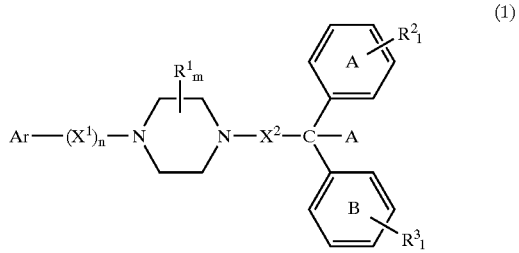

(1)

wherein Ar is phenyl, a six-membered or five-membered ring which is heteroaromatic or a fused aromatic or heteroaromatic system, each of which may optionally be substituted with one or more non-interfering substituents;

$X^1$ is a linker containing 1–5 members;

n is 0 or 1;

each $R^1$–$R^3$ is independently a non-interfering non-hydrogen substituent;

each l is independently 0–5;

m is 0–4;

$X^2$ is a linker comprising a chain of at least 5 members;

A is H, OR, SR, $NR_2$, or halo wherein R is H or lower alkyl (1–6C);

with the proviso that (a) Ar is an optionally substituted five- or six-membered heteroaryl substituent or an optionally substituted fused aromatic or heteroaromatic substituent; and/or (b) n is 0; and/or (c) m is 1–4; and/or (d) $X^2$ is alkylene substituted by =O, OR, SR, $NR_2$ and/or halo; and/or (e) $X^2$ is a chain of at least 6 members; and/or (f) $X^2$ contains at least one heteroatom selected from N, S and O; and/or (g) A is OR, SR, $NR_2$ or halo, wherein R is H or lower alkyl (1–6C) and/or (h) Ar is substituted with at least one t-butyl moiety or at least one substituted alkoxy; and/or (i) $X^1$ includes at least one heteroatom selected from O, N and S.

In one set of preferred embodiments, the compounds are of the formula:

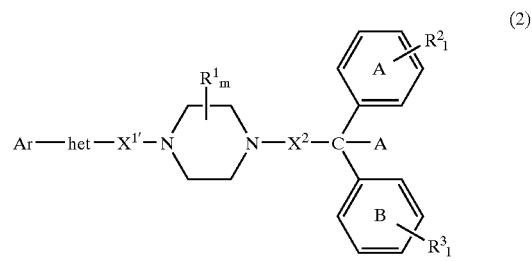

(2)

wherein Ar, $X^1$, $R^{2-R3}$, l, m, $X^2$ and A are as defined above, "het" is a heteroatom selected from O, S and N, and $X^{1'}$ is defined as $X^1$ less one chain member.

In another embodiment, the compounds of the invention are of formula

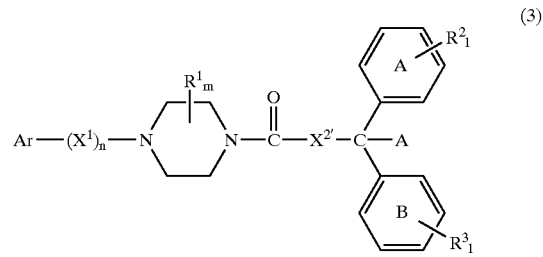

(3)

wherein Ar, $X^1$, $R^{1-R3}$, l, m, n, A and Ar are defined as above, and $X^{2'}$ is defined as $X^2$ less one chain member.

In still another embodiment, the invention is directed to the compounds of formula

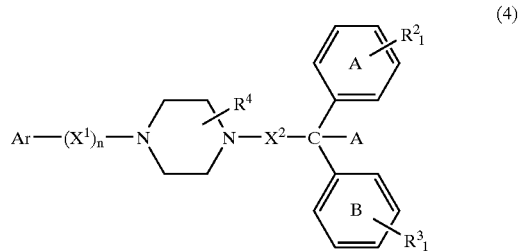

(4)

wherein $R^4$ is a carboxylic acid group or ester or amide thereof and Ar, $R^{2-R3}$, $X^1$, l, n, $X^2$ and A are defined as above.

The substituents $R^1$–$R^3$, the substituents on Ar and on substituted alkoxy in (h) are each independently optionally substituted alkyl (1–10C), alkenyl (2–10C), alkynyl (2–10C), aryl (6–10C), arylalkyl (7–16C) or arylalkenyl (7–16C) each optionally further containing 1–4 heteroatoms (N, O or S) and wherein said optional substituents on alkyl, alkenyl, etc., may include one or more =O thus including embodiments wherein these substituents may independently form an acyl, amide, or ester linkage with the atom to which it is bound. The substituents $R^{1-R3}$, on Ar or on substituted alkoxy independently include, as well, one or more halo, $CF_3$, CN, OCF, $NO_2$, $NR_2$, OR, SR, COOR, and/or $CONR_2$, wherein R is H or optionally substituted alkyl, alkenyl, alkynyl, aryl, arylalkyl, or arylalkenyl, as described above, and wherein S may be oxidized, and wherein two substituents at adjacent positions on the same ring may form a 3–7 membered saturated or unsaturated ring fused to said substituted ring, said fused ring optionally itself substituted and optionally containing one or more heteroatoms (N, S, O) and wherein said fused ring may further be fused to an additional aromatic moiety, as shown, for instance, in compound P35.

Alternatively, a combination of $R^2$ and $R^3$ may form a bond or a bridge between the phenyl groups on which they reside—e.g., $R^2$ and $R^3$ together may be a bond or one or more $CR_2$ groups, an NR group, an O, or S wherein the S is optionally oxidized, or combinations thereof.

The invention is also directed to methods to modulate calcium channel activity, preferably N-type and T-type channel activity, using the compounds of formula (1) and thus to treat certain undesirable physiological conditions; these conditions are associated with abnormal calcium channel activity. In another aspect, the invention is directed to pharmaceutical compositions containing these compounds, and to the use of these compounds for the preparation of medicaments for the treatment of conditions requiring modulation of calcium channel activity.

MODES FOR CARRYING OUT THE INVENTION

Figure 1:
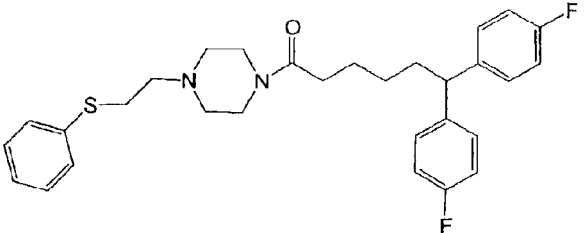
FIG. 1 shows illustrative compounds of the invention.
Figure 1:
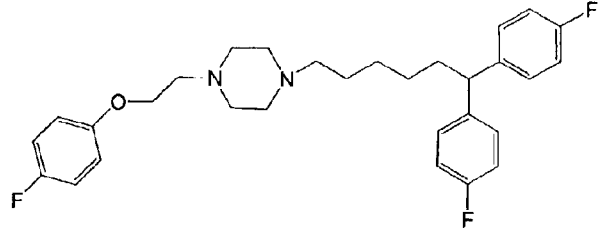
Figure 1:
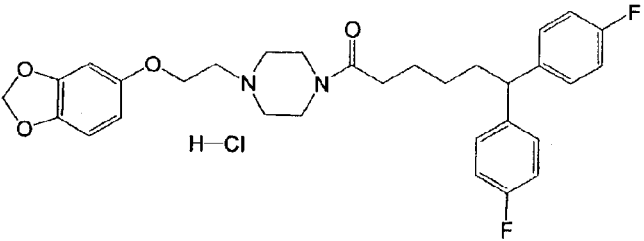
Figure 1:
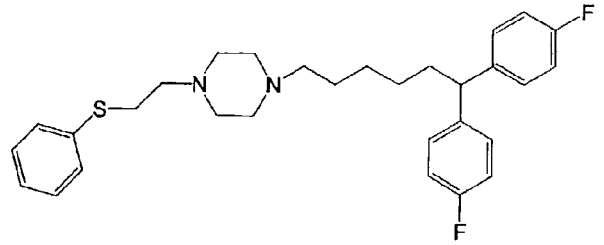
Figure 1:
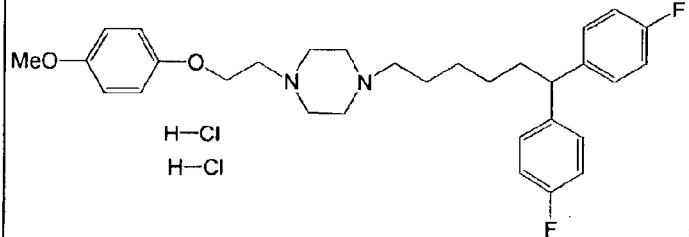
Figure 1:
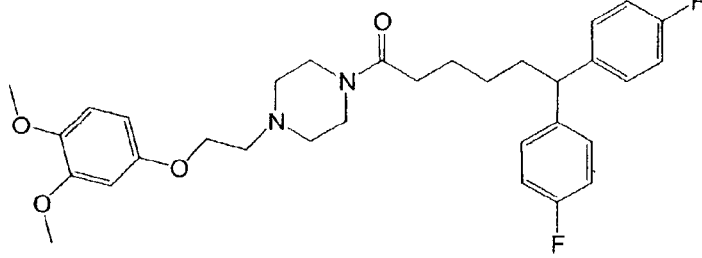
Figure 1:
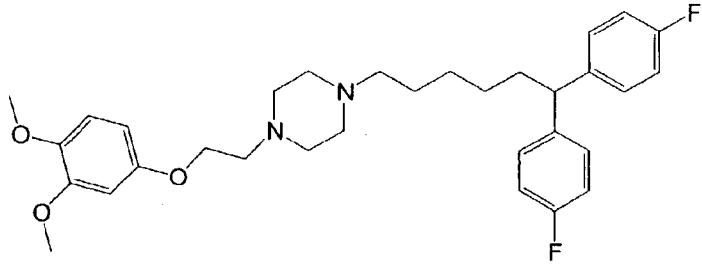

The compounds of formula (1) useful in the methods of the invention exert their desirable effects through their ability to modulate the activity of N-type and/or T-type calcium channels. This makes them useful for treatment of certain conditions. Among such conditions where antagonist activity is desired are stroke, anxiety, epilepsy, head trauma, migraine, inflammatory bowel disease, overactive bladder and chronic, neuropathic and acute pain. Calcium flux is also implicated in other neurological disorders such as schizophrenia, anxiety, depression, other psychoses, neural degenerative disorders and drug and alcohol addiction and withdrawal. Other treatable conditions include cardiovascular conditions such as hypertension and cardiac arrhythmias. In addition, T-type calcium channels have been implicated in certain types of cancer, diabetes infertility and sexual dysfunction.

While the compounds of formula (1) generally have this activity, availability of this class of calcium channel modulators permits a nuanced selection of compounds for particular disorders. The availability of this class of compounds provides not only a genus of general utility in indications that are affected by calcium channel activity, but also provides a large number of compounds which can be mined and manipulated for specific interaction with particular forms of calcium channels. The availability of recombinantly produced calcium channels of the $\alpha_{1A}$–$\alpha_{1I}$ and $\alpha_{1S}$ types set forth above, facilitates this selection process. Dubel, S. J., et al., *Proc. Natl. Acad. Sci. USA* (1992) 89:5058–5062; Fujita, Y., et al., *Neuron* (1993) 10:585–598; Mikami, A., et al., *Nature* (1989) 340:230–233; Mori, Y., et al., *Nature* (1991) 350:398–402; Snutch, T. P., et al., *Neuron* (1991) 7:45–57; Soong, T. W., et al., *Science* (1993) 260:1133–1136; Tomlinson, W. J., et al., *Neuropharmacology* (1993) 32:1117–1126; Williams, M. E., et al., *Neuron* (1992) 8:71–84; Williams, M. E., et al., *Science* (1992) 257:389–395; Perez-Reyes, et al., *Nature* (1998) 391:896–900; Cribbs, L. L., et al., *Circulation Research* (1998) 83:103–109; Lee, J. H., et al., *Journal of Neuroscience* (1999) 19:1912–1921; McRory, J. E., et al., *Journal of Biological Chemistry* (2001) 276:3999–4011.

It is known that calcium channel activity is involved in a multiplicity of disorders, and particular types of channels are associated with particular conditions. The association of N-type and T-type channels in conditions associated with neural transmission would indicate that compounds of the invention which target N-type receptors are most useful in these conditions. Many of the members of the genus of compounds of formula (1) exhibit high affinity for N-type channels and/or T-type channels. Thus, as described below, they are screened for their ability to interact with N-type and/or T-type channels as an initial indication of desirable function. It is desirable that the compounds exhibit $IC_{50}$ values of <1 μM. The $IC_{50}$ is the concentration which inhibits 50% of the calcium, barium or other permeant divalent cation flux at a particular applied potential.

There are three distinguishable types of calcium channel inhibition. The first, designated "open channel blockage," is conveniently demonstrated when displayed calcium channels are maintained at an artificially negative resting potential of about –100 mV (as distinguished from the typical endogenous resting maintained potential of about –70 mV). When the displayed channels are abruptly depolarized under these conditions, calcium ions are caused to flow through the channel and exhibit a peak current flow which then decays. Open channel blocking inhibitors diminish the current exhibited at the peak flow and can also accelerate the rate of current decay.

This type of inhibition is distinguished from a second type of block, referred to herein as "inactivation inhibition." When maintained at less negative resting potentials, such as the physiologically important potential of –70 mV, a certain percentage of the channels may undergo conformational change, rendering them incapable of being activated—i.e., opened—by the abrupt depolarization. Thus, the peak current due to calcium ion flow will be diminished not because the open channel is blocked, but because some of the channels are unavailable for opening (inactivated). "Inactivation" type inhibitors increase the percentage of receptors that are in an inactivated state.

A third type of inhibition is designated "resting channel block". Resting channel block is the inhibition of the channel that occurs in the absence of membrane depolarization, that would normally lead to opening or inactivation. For example, resting channel blockers would diminish the peak current amplitude during the very first depolarization after drug application without additional inhibition during the depolarization.

In order to be maximally useful in treatment, it is also helpful to assess the side reactions which might occur. Thus, in addition to being able to modulate a particular calcium channel, it is desirable that the compound has very low activity with respect to the HERG $K^+$ channel which is expressed in the heart. Compounds that block this channel with high potency may cause reactions which are fatal. Thus, for a compound that modulates the calcium channel, it should also be shown that the HERG K$^+$ channel is not inhibited. Similarly, it would be undesirable for the compound to inhibit cytochrome p450 since this enzyme is required for drug detoxification. Finally, the compound will be evaluated for calcium ion channel type specificity by comparing its activity among the various types of calcium channels, and specificity for one particular channel type is preferred. The compounds which progress through these tests successfully are then examined in animal models as actual drug candidates.

The compounds of the invention modulate the activity of calcium channels; in general, said modulation is the inhibition of the ability of the channel to transport calcium. As described below, the effect of a particular compound on calcium channel activity can readily be ascertained in a routine assay whereby the conditions are arranged so that the channel is activated, and the effect of the compound on this activation (either positive or negative) is assessed. Typical assays are described hereinbelow.

The Invention Compounds

The substituents on the basic structures of formulas (1)–(4) are described above. These include alkyl, alkenyl, alkynyl, etc., substituents.

As used herein, the term "alkyl," "alkenyl" and "alkynyl" include straight-chain, branched-chain and cyclic monovalent substituents, containing only C and H when they are unsubstituted or unless otherwise noted. Examples include methyl, ethyl, isobutyl, cyclohexyl, cyclopentylethyl, 2-propenyl, 3-butynyl, and the like. Typically, the alkyl, alkenyl and alkynyl substituents contain 1–10C (alkyl) or 2–10C (alkenyl or alkynyl). Preferably they contain 1–6C (lower alkyl) or 2–6C (lower alkenyl or lower alkynyl).

Heteroalkyl, heteroalkenyl and heteroalkynyl are similarly defined but may contain one or more O, S or N heteroatoms or combinations thereof within the backbone residue.

As used herein, "acyl" encompasses the definitions of alkyl, alkenyl, alkynyl, each of which is coupled to an additional residue through a carbonyl group. Heteroacyl includes the related heteroforms.

"Aromatic" moiety or "aryl" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Any monocyclic or fused ring bicyclic system which has the characteristics of aromaticity in terms of electron distribution throughout the ring system is included in this definition. Typically, the ring systems contain 5–12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1–8C, or the hetero forms thereof. These carbon chains may also include a carbonyl group, thus making them able to provide substituents as an acyl or heteroacyl moiety.

In general, any alkyl, alkenyl, alkynyl, acyl, or aryl group contained in a substituent may itself optionally be substituted by additional substituents. The nature of these substituents is similar to those recited with regard to the primary substituents themselves. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments. However, alkyl substituted by aryl, amino, alkoxy, and the like would be included.

Non-interfering substituents in general include, but are not limited to, alkyl, alkenyl, alkynyl, aryl, arylalkyl, acyl, =O, halo, OR, NR$_2$, SR, —SOR, —SO$_2$R, —OCOR, —NRCOR, —NRCONR$_2$, —NRCOOR, —OCONR$_2$, —RCO, —COOR, SO$_2$R, NRSOR, NRSO$_2$R, —SO$_3$R, —CONR$_2$, SO$_2$NR$_2$, wherein each R is independently H or alkyl (1–8C), —CN, —CF$_3$, and NO$_2$, and like substituents.

In the compounds of the invention, Ar is preferably optionally substituted phenyl, 2-, 3- or 4-pyridyl, indolyl, 2- or 4-pyrimidyl, pyridazinyl, benzotriazolyl or benzimidazolyl. More preferably Ar is phenyl, pyridyl, or pyrimidyl. Most preferably Ar is phenyl. Each of these embodiments may optionally be substituted with a group defined above such as alkyl, alkenyl, alkynyl, aryl, O-aryl, O-alkylaryl, O-aroyl, NR-aryl, N-alkylaryl, NR-aroyl, halo, OR, NR$_2$, SR, —OOCR, —NROCR, RCO, —COOR, —CONR$_2$, and/or SO$_2$NR$_2$, wherein each R is independently H or alkyl (1–8C), and/or by —CN, —CF$_3$, and/or NO$_2$. Alkyl, alkenyl, alkynyl and aryl portions of these may be further substituted by similar substituents.

Among preferred substituents on Ar are tert-butyl, methoxy, substituted alkoxy, hydroxy and halo. Preferred embodiments of R$^1$ include =O and carboxy. Preferred embodiments of R$^2$ and R$^3$ include alkoxy, halo, and alkyl.

The linker X$^1$ may or may not be present. When present, it typically has 1–5 members in the chain linking the piperazine ring to Ar. Preferred forms are alkylene, optionally including one or more, preferably one, heteroatom selected from O, S and N. Preferably, but not necessarily, the heteroatom is adjacent the aromatic group as shown in formula (2). In many embodiments, X$^1$ includes =O, preferably adjacent the piperazine ring.

The linker X$^2$ must be present and contains at least 5 members in the chain. In many embodiments, X$^2$ contains =O substituted adjacent the piperazine ring. X$^2$ may further contain one or more heteroatom, preferably one heteroatom selected from N, S and O and may further contain substituents such as OR, SR, NR$_2$ and/or halo.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Suitable pharmaceutically acceptable acids and bases are well-known in the art, such as hydrochloric, sulphuric, citric, acidic, or tartaric acids and potassium hydroxide, sodium hydroxide, ammonium hydroxide, caffeine, various amines, and the like. Methods for preparation of the appropriate salts are well-established in the art.

In addition, in some cases, the compounds of the invention contain one or more chiral centers. The invention includes the isolated stereoisomeric forms as well as mixtures of stereoisomers in varying degrees of chiral purity.

Synthesis of the Invention Compounds

The compounds of the invention may be synthesized using conventional methods. Illustrative of such methods are Schemes 1–5:

Reaction Scheme 1 is used to prepare compounds of the invention with keto substituent in X$^1$ and X$^2$. By modifying the substituents on the phenyl ring contained in formula (1) above, variations of the P44 and P46 products shown can be made.

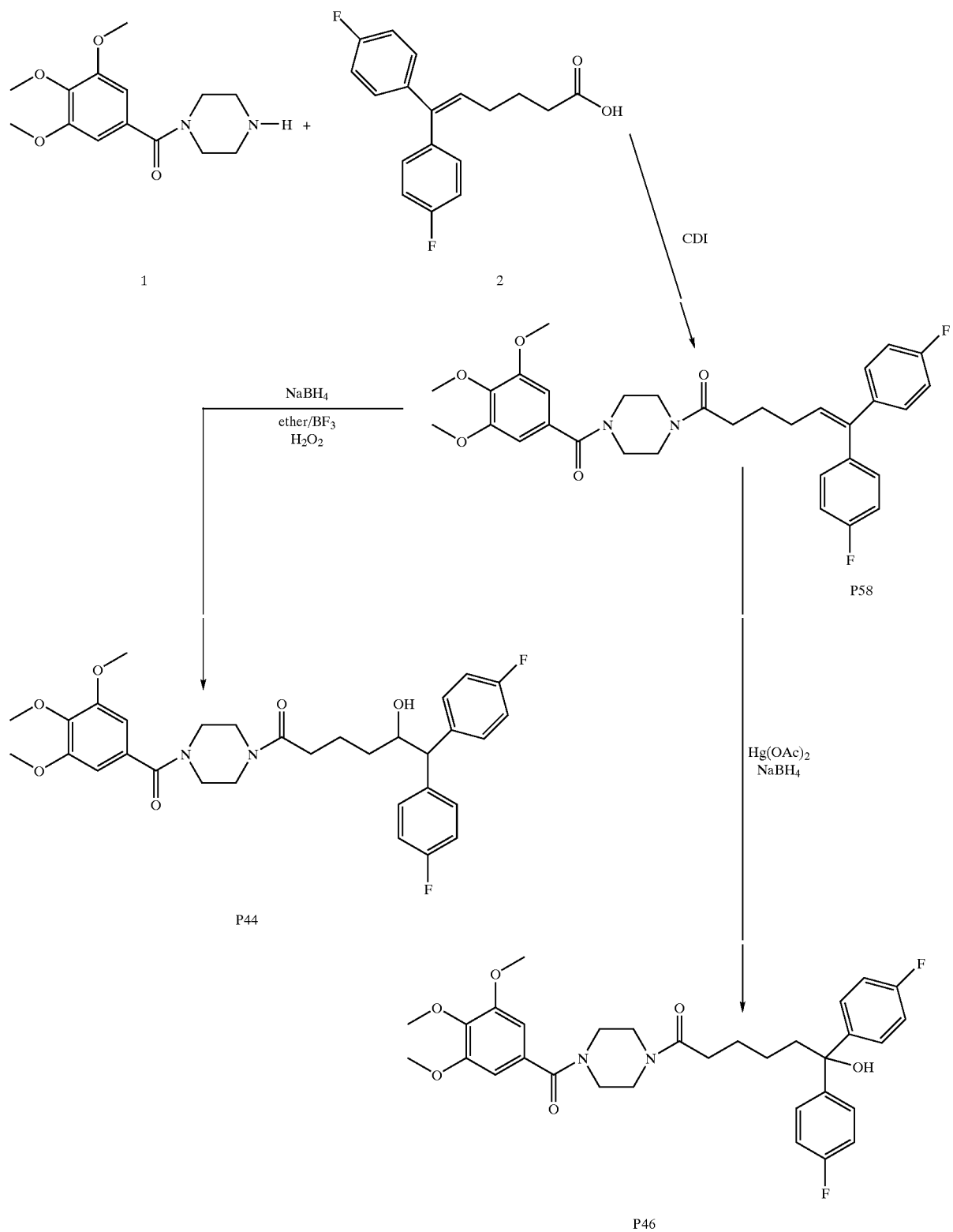

Reaction Scheme 1

Reaction Scheme 2 is used to prepare compounds of the invention within the embodiment of formula (2). Variations in R, and substitutions for the fluoro substituents in compound 6 will result in variants having corresponding variations in the compounds shown as 8 above. In particular, compounds P1, P2, P3, P4, P5, P6, P7, P8, P39, P9, P10, P11, P12, P13, P14 and P15 may be synthesized using this approach.

Reaction Scheme 2
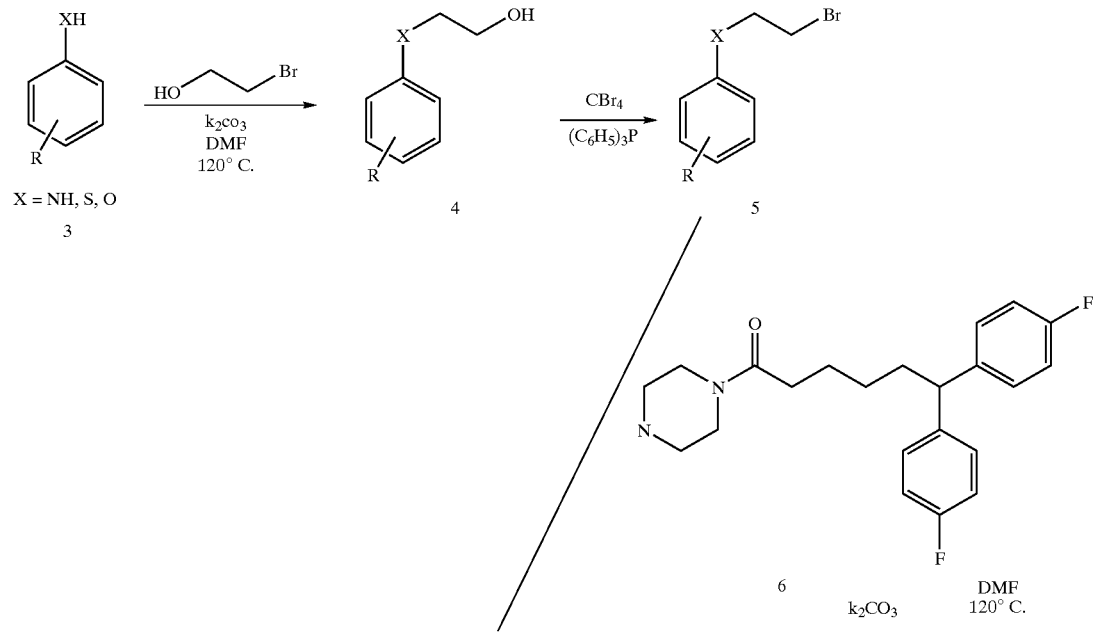
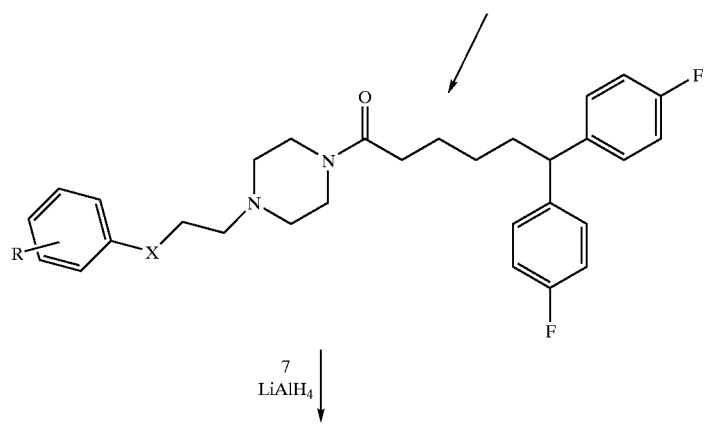
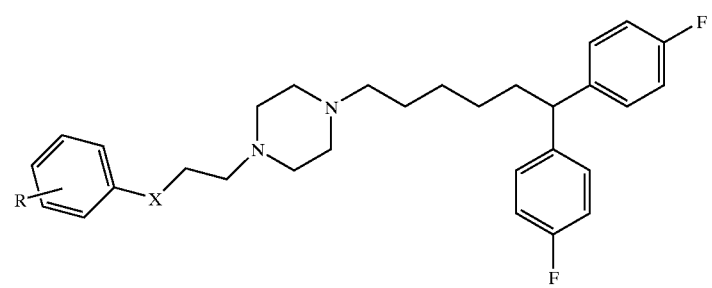

Reaction Scheme 3 shows synthesis of compounds of the invention which comprise tertiary butyl substituents in Ar.
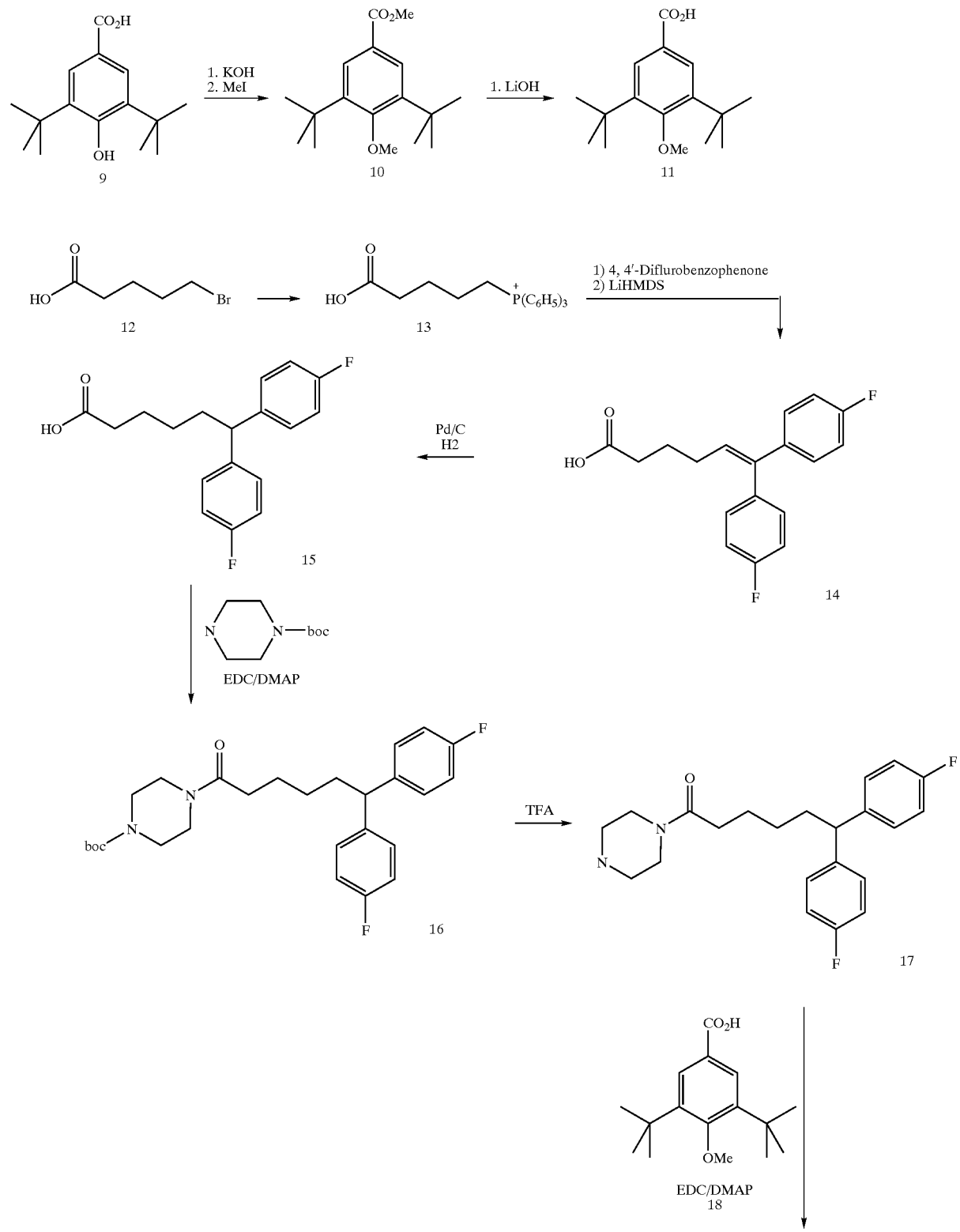

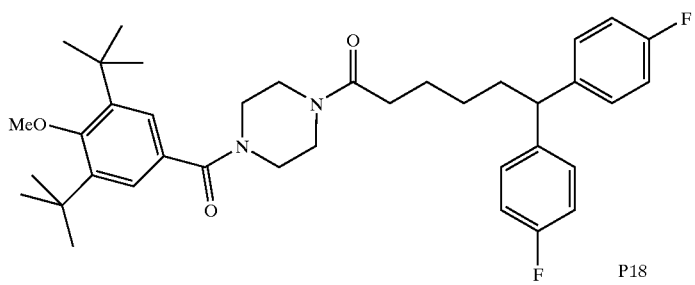
Reaction Scheme 4 shows synthesis of compounds of the invention which comprise a keto substitution on the piperazine ring, such as in compounds P48–P57.
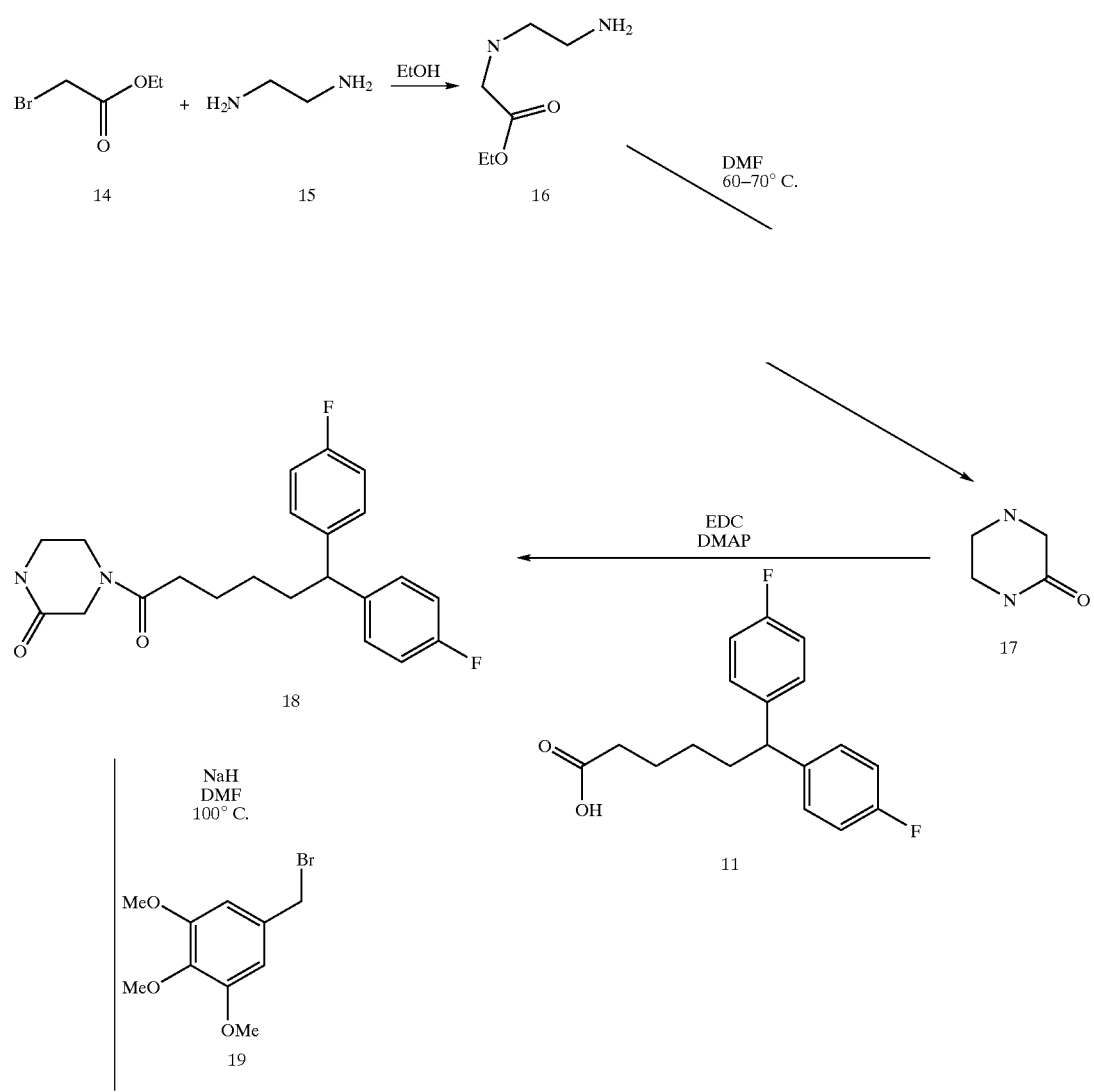

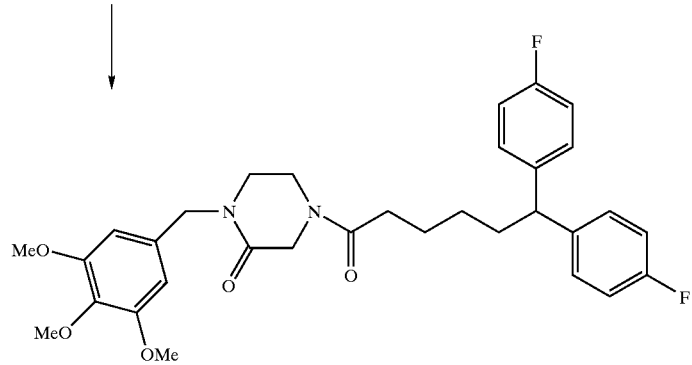
Reaction Scheme 5 shows synthesis of compounds of the invention which comprise a various substitutions on the piperazine ring, such as in compounds P36 and P47.
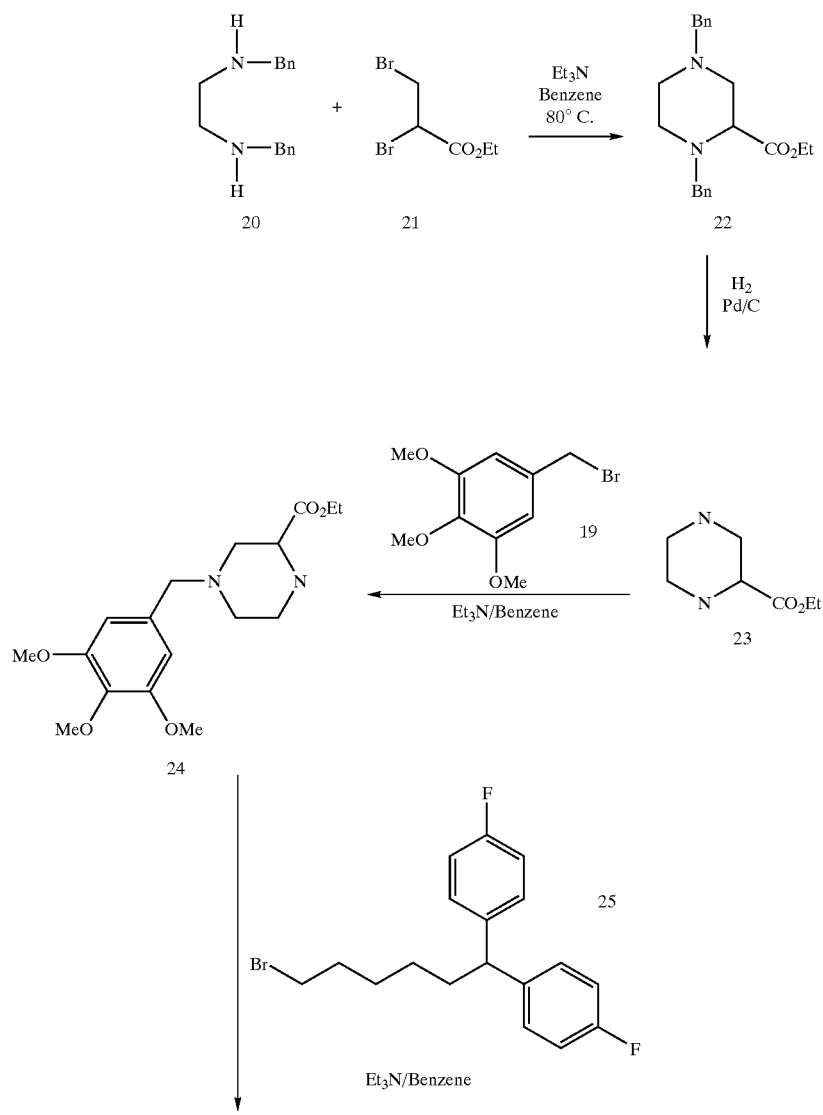

-continued

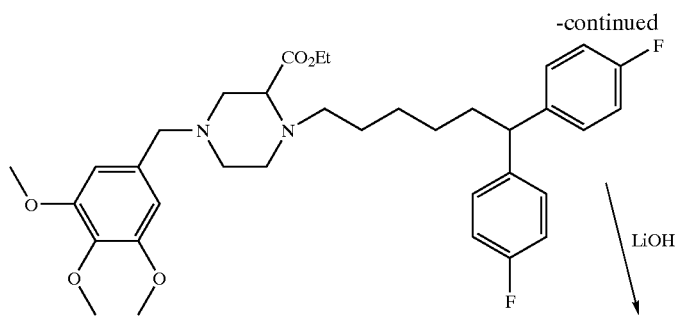

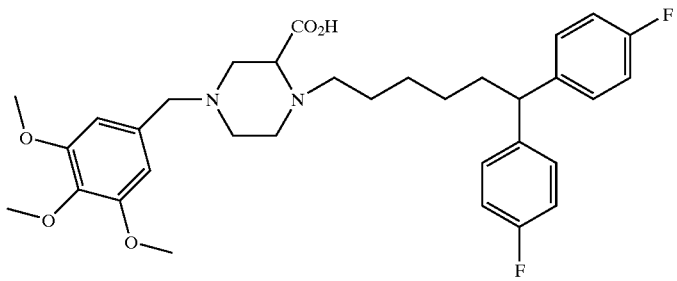

P47

Libraries and Screening

The compounds of the invention can be synthesized individually using methods known in the art per se, or as members of a combinatorial library.

Synthesis of combinatorial libraries is now commonplace in the art. Suitable descriptions of such syntheses are found, for example, in Wentworth, Jr., P., et al., *Current Opinion in Biol.* (1993) 9:109–115; Salemme, F. R., et al., *Structure* (1997) 5:319–324. The libraries contain compounds with various substituents and various degrees of unsaturation, as well as different chain lengths. The libraries, which contain, as few as 10, but typically several hundred members to several thousand members, may then be screened for compounds which are particularly effective against a specific subtype of calcium channel, i.e., the N-type channel. In addition, using standard screening protocols, the libraries may be screened for compounds which block additional channels or receptors such as sodium channels, potassium channels and the like.

Methods of performing these screening functions are well known in the art. These methods can also be used for individually ascertaining the ability of a compound to agonize or antagonize the channel. Typically, the channel to be targeted is expressed at the surface of a recombinant host cell such as human embryonic kidney cells. The ability of the members of the library to bind the channel to be tested is measured, for example, by the ability of the compound in the library to displace a labeled binding ligand such as the ligand normally associated with the channel or an antibody to the channel. More typically, ability to antagonize the channel is measured in the presence of calcium, barium or other permeant divalent cation and the ability of the compound to interfere with the signal generated is measured using standard techniques. In more detail, one method involves the binding of radiolabeled agents that interact with the calcium channel and subsequent analysis of equilibrium binding measurements including, but not limited to, on rates, off rates, $K_d$ values and competitive binding by other molecules.

Another method involves the screening for the effects of compounds by electrophysiological assay whereby individual cells are impaled with a microelectrode and currents through the calcium channel are recorded before and after application of the compound of interest.

Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel or as resting channel blockers. The methods to distinguish these types of inhibition are more particularly described in the examples below. In general, open-channel blockers are assessed by measuring the level of peak current when depolarization is imposed on a background resting potential of about −100 mV in the presence and absence of the candidate compound. Successful open-channel blockers will reduce the peak current observed and may accelerate the decay of this current. Compounds that are inactivated channel blockers are generally determined by their ability to shift the voltage dependence of inactivation towards more negative potentials. This is also reflected in their ability to reduce peak currents at more depolarized holding potentials (e.g., −70 mV) and at higher frequencies of stimulation, e.g., 0.2 Hz vs. 0.03 Hz. Finally, resting channel blockers would diminish the peak current amplitude during the very first depolarization after drug application without additional inhibition during the depolarization.

Utility and Administration

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in Remington's *Pharmaceutical Sciences*, latest edition, Mack Publishing Co., Easton, Pa., incorporated herein by reference.

In general, for use in treatment, the compounds of formula (1) may be used alone, as mixtures of two or more compounds of formula (1) or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the dosage of the compounds of the invention is typically 0.1–15 mg/kg, preferably 0.1–1 mg/kg. However, dosage levels are highly dependent on the nature of the condition, drug efficacy, the condition of the patient, the judgment of the practitioner, and the frequency and mode of administration.

The following examples are intended to illustrate but not to limit the invention.

EXAMPLE 1

Synthesis of 6,6-bis-(4-fluoro-phenyl)-1-[4-(3,4,5,-trimethoxy-benzoyl)-piperazin-1-yl]-hex-5-en-1-one (P58)

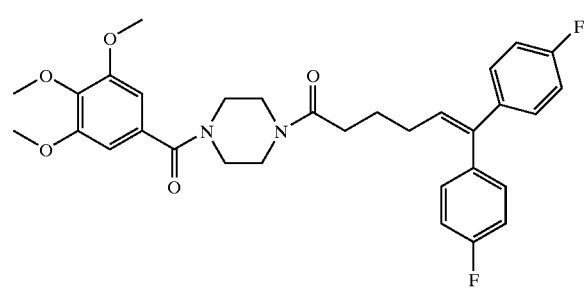

A solution of 6,6-bis-(4-fluoro-phenyl)-hex-5-enoic acid (2.64 g, 8.75 mmol) and CDI (1.42 g, 8.75 mmol) in dry THF (30 ml) was stirred for 1 hr at room temperature under nitrogen. A solution of piperazin-1-yl-(3,4,5,-trimethoxy-phenyl)-methanone (2.45 g, 8.75 mmol) in dry THF (30 ml) was added to above solution and resulting mixture stirred at room temperature overnight. The mixture is diluted with EtOAc (30 ml) and washed with water (2×30 ml) and dried over MgSO$_4$. Evaporation of solvent followed by column chromatography using CH$_2$Cl$_2$:MeOH (15:1) gave the desired product in 49% yield.

EXAMPLE 2

Synthesis of 6,6-bis-(4-fluoro-phenyl)-5-hydroxy-1-[4-(3,4,5,-trimethoxy-benzoyl)-piperazin-1-yl]-hexan-1-one (P44)

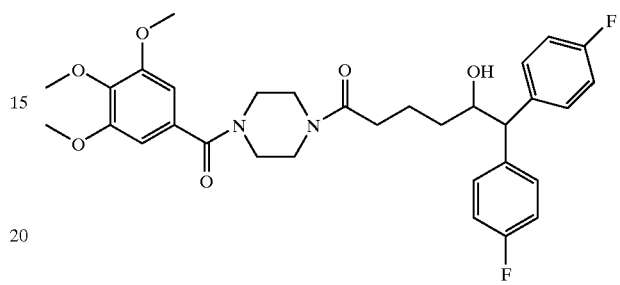

To a solution of 6,6-bis-(4-fluoro-phenyl)-1-[4-(3,4,5,-trimethoxy-benzoyl)-piperazin-1-yl]-hex-5-en-1-one (1.3 g, 2.3 mmol) in dry THF (20 ml) was added NaBH$_4$ (22 mg, 0.58 mmol) followed by dropwise addition of BF$_3$.Et$_2$O (0.2 ml, 1.43 mmol). The resulting mixture stirred at r.t. for 3 hrs and excess NaBH$_4$ decomposed by addition of water(0.1 ml). The mixture was then oxidized by adding 3M NaOH (0.3 ml) followed by addition of H$_2$O$_2$ (0.5 ml, 3 mmol). After stirring for 1.5 hrs at 30–40° C., the mixture was washed with brine (30 ml). The organic layer dried over MgSO$_4$ and evaporated. The residue was purified by column chromatography using EtOAc:hexane (3:1) to give the desired product in 64% yield.

EXAMPLE 3

Synthesis of 6,6-bis-(4-fluoro-phenyl)-6-hydroxy-1-[4-(3,4,5,-trimethoxy-benzoyl)-piperazin-1-yl]-hexan-1-one (P46)

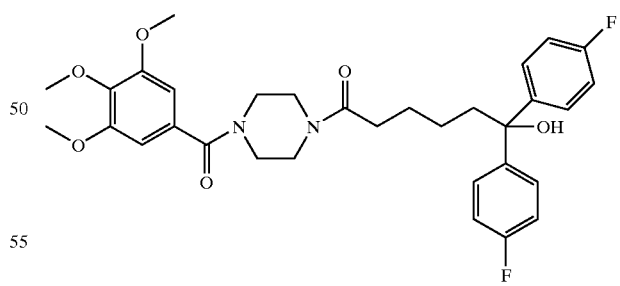

To a solution of 6,6-bis-(4-fluoro-phenyl)-1-[4-(3,4,5,-trimethoxy-benzoyl)-piperazin-1-yl]-hex-5-en-1-one (1.62 g, 2.87 mmol) in dry THF (20 ml) a solution of Hg(OAc)$_2$ (0.9 g, 2.87 mmol) in water:THF (1:1, 6 ml) was added. The mixture was then refluxed overnight. NaOH (3M, 3 ml) was added followed by addition of NaBH$_4$ (54 mg, 1.43 mmol). The mixture was stirred for 4 hrs and separated organic layer was saturated with NaCl

EXAMPLE 4

Synthesis of 1-{4-[2-(3,4-dimethoxy-phenoxy)ethyl]-piperazin-1-yl}-6,6-bis-(4-fluoro-phenyl)-hexan-1-one (P59)

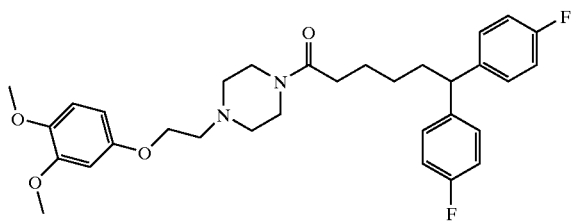

A. Synthesis of 2-(3,4-dimethoxy-phenoxy)-ethanol

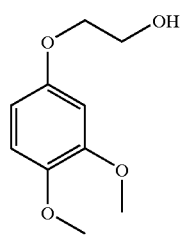

K₂CO₃ (1.07 g, 7.78 mmol) was added to a solution of 3,4,dimethoxyphenol (1.0 g, 6.48 mmol) in dry DMF (15 ml). 2-Bromoethanol (0.81 g, 6.48 mmol) was added, and the mixture was heated overnight at 120° C. The mixture was cooled, taken up in EtOAc, extracted with water (20 ml), saturated NaCl (4×20 ml), dried over MgSO₄, and evaporated under reduced pressure. The product was purified by column chromatography on silica (Hexane:EtOAc 3:1) to give the desired product in 60% yield.

B. Synthesis of 4-(2-bromo-ethoxy)-1,2-dimethoxy benzene

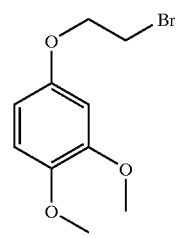

To a cool solution of 2-(3,4-dimethoxy-phenoxy)-ethanol (0.55 g, 2.77 mmol.) in CH₂Cl₂ (15 ml), triphenyl phosphine (1.3 g, 5 mmol)) was added. Carbon tetrabromide (1.65 g, 5 mmol.) in CH₂Cl₂ (3 ml) was added to the solution dropwise under N₂. The solution was stirred for 30 minutes. EtOAc was added, then the solvent was evaporated under reduced pressure. The product was purified by column chromatography on silica (Hexane:EtOAc 1:1) to give the desired product in 85% yield.

C. Synthesis of 1-{4-[2-(3,4-dimethoxy-phenoxy)ethyl]-piperazin-1-yl}-6,6-bis-(4-fluoro-phenyl)-hexan-1-one (P59)

To a solution of 4-(2-bromo-ethoxy)-1,2-dimethoxy benzene (1.41 g, 4.86 mmol) and 6,6-bis-(4-fluorophenyl)-1-piperazin-1-yl-hexan-1-one (1.81 g, 4.86 mmol.) in dry DMF (40 ml) was added K₂CO₃ (0.8 g, 5.83 mmol.) and the mixture stirred at 120° C. overnight. EtOAc was added, washed with water (2×30 ml), brine (3×10 ml), dried over MgSO₄, and evaporated under reduced pressure. The produce was purified by column chromatography on silica (hexane:EtOAc 1:1), followed by EtOAc to give the desired product in 57% yield.

EXAMPLE 5

Synthesis of 1-[6,6-bis-(4-fluoro-phenyl)-hexyl]-4-[2-(3,4-dimethoxy-phenoxy)-ethyl]-piperazine (P60)

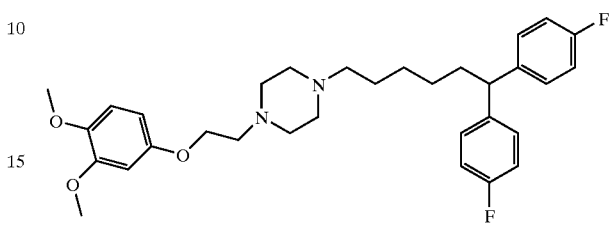

To a solution of 1-{4-[2-(3,4-dimethoxy-phenoxy)ethyl]-piperazin-1-yl}-6,6-bis-(4-fluoro-phenyl)-hexan-1-one (0.7 g, 1.2 mmol) in THF (15 ml), was added LiAlH₄ (100 mg, 2.4 mmol). The mixture was stirred at room temperature overnight (under N₂). EtOAc was added and then washed with wate (2×10 ml), saturated NaCl (3×5 ml), dried over MgSO₄, and evaporated under reduced pressure. The residue was purified by column chromatography on silica (CH₂Cl₂:MeOH 10:1) to give the desired product in 73% yield.

EXAMPLE 6

Synthesis of 1-[4-(3,5-di-tert-butyl-4-methoxy-benzoyl)-piperazi-1-yl]-6,6-bis-(4-fluoro-phenyl)-hexan-1-one (P18)

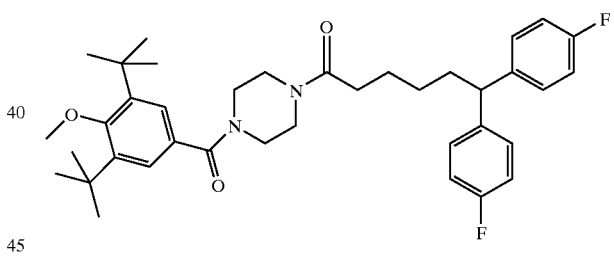

A. Synthesis of 3,5-di-tert-butyl-4-methoxy-benzoic acid methyl ester

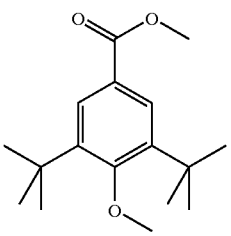

3,5-Di-tert-butyl-4-hydroxy-benzoic acid (0.7 g, 2.79 mmol) was added to a solution of KOH (313 mg, 5.59 mmol) in dry acetone (8 ml) and resulting mixture stirred at room temperature overnight until all KOH were dissolved. MeI (0.41 ml, 6.69 mmol) was then added and the mixture refluxed for 24 hours. Water (8 ml) was then added and aqueous phase extracted with ether (2×). The organic phase was then washed with 10% NaOH (1×), water (1×), saturated NH$_4$Cl and dried over MgSO$_4$. Purification using hexane:ethyl acetate, 30:1, gave 0.6 g of pure product.

B. Synthesis of 3,5-di-tert-butyl-4-methoxy-benzoic acid

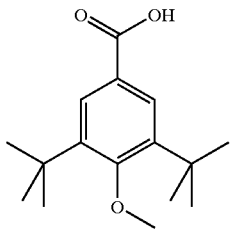

A mixture of 3,5-di-tert-butyl-4-methoxy-benzoic acid methyl ester (0.56 g, 2.01 mmol) and LiOH (253 mg, 6.03 mmol) in THF:MeOH:H$_2$O (3:1:1, 50 ml) stirred at room temperature for 2 days. The solvent was then evaporated and residue dissolved in water and acidified with 2N HCl to pH 3. The aqueous phase was then extracted with EtOAc and organic phase was dried over MgSO$_4$. Upon evaporation 0.51 g of pure product was isolated.

C. Synthesis of 4-[6,6-bis-(4-fluoro-phenyl)-hexanoyl]-piperazine-1-carboxylic acid tert-butyl ester

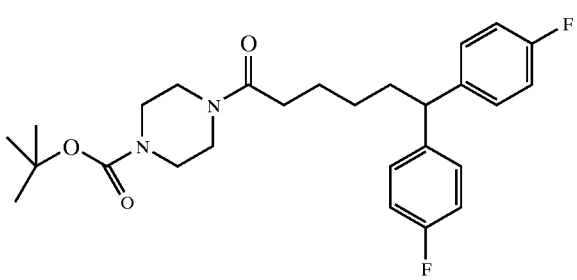

To a solution of 6,6-bis-(4-fluoro-phenyl)-hexanoic acid (2.94 g, 9.66 mmol) in dry CH$_2$Cl$_2$ (80 ml) was added mono-boc piparizine (1.98 g, 10.63 mmol) under nitrogen. To the reaction was added EDC (4.07 g, 21.26 mmol) and DMAP (cat) and the reaction mixture stirred under nitrogen at room temperature overnight. The reaction was then concentrated under reduced pressure. The residue dissolved in ethyl acetate:water (10:1) (250 ml). The organic was washed with water (50 ml, 2×) and 10% NaOH (50 ml) and dried over MgSO$_4$ and evaporated to dryness. The resulting residue was purified by column chromatography using hexane: ethyl acetate (1:1) to give desired product in 78% yield.

D. Synthesis of 6,6-bis-(4-fluoro-phenyl)-1-piperazin-1-yl-hexan-1-one

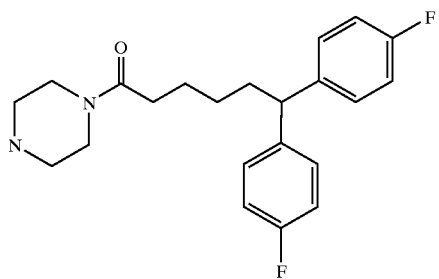

To a solution of 4-[6,6-bis-(4-fluoro-phenyl)-hexanoyl]-piperazine-1-carboxylic acid tert-butyl ester (4.25 g, 8.99 mmol) in dry CH$_2$Cl$_2$ (100 ml) was added TFA (32 ml) and resulting mixture stirred at room temperature for 3 hrs. Solvent and excess TFA was then evaporated and the residue was dissolved in CH$_2$Cl$_2$ (150 ml) and washed with sat. NaHCO$_3$ (2×) and dried over MgSO$_4$. Evaporation of solvent gave 3.9 g of pure product.

E. Synthesis of 1-[4-(3,5-di-tert-butyl-4-methoxy-benzoyl)-piperazi-1-yl]-6,6-bis-(4-fluoro-phenyl)-hexan-1-one (P18)

To a solution of 6,6-bis-(4-fluoro-phenyl)-1-piperazin-1-yl-hexan-1-one (1.41 g, 3.78 mmol) in dry CH$_2$Cl$_2$ (60 ml) was added 3,5-di-tert-butyl-4-methoxy-benzoic acid (0.91 g, 3.44 mmol) under nitrogen. To the reaction was added EDC (1.45 g, 7.57 mmol) and DMAP (cat) and the reaction mixture stirred under nitrogen at room temperature overnight. The reaction was then concentrated under reduced pressure. The residue dissolved in ethyl acetate:water (10:1) (100 ml). The organic was washed with water (30 ml, 2×) and 10% NaOH (30 ml) and dried over MgSO$_4$ and evaporated to dryness. The resulting residue was purified by column chromatography using hexane:ethyl acetate (1:2) to give desired product in 76% yield.

EXAMPLE 7

Synthesis of 4-[6,6-bis-(4-fluoro-phenyl)-hexanoyl]-1-(3,4,5-trimethoxy-benzyl)-piperazin-2-one (P48)

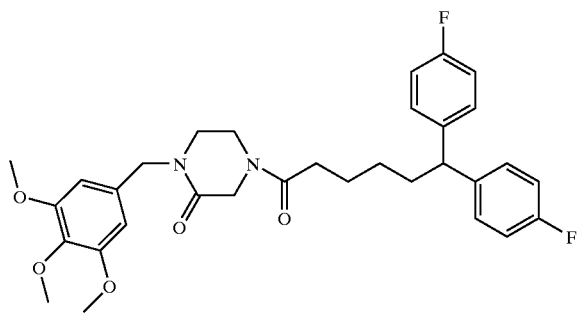

A. Synthesis of 2-ketopiperazine

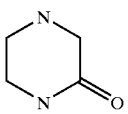

A solution of bromoethylacetate (10 g, 59.8 mmol) in absolute ethanol (80 ml) is slowly added at room temperature to a solution of ethylenediamine (36 g, 598 mmol) in absolute ethanol (140 ml). The addition requires about three hours and the mixture is allowed to stand for an additional two hours. Sodium ethoxide (21% wt, 22 ml, 59.8 mmol) was added dropwise. The mixture was stirred at room temperature overnight and solvent was then evaporated. DMF (40 ml) was added to residue and stirred at 60–70° C. for 24 hours. The salt was filtered and the solvent was evaporated. The residue was purified by column chromatography using CH$_2$Cl$_2$: MeOH:NH$_4$OH (90:10:0.1) to give a yellow solid in 45% yield.

B. Synthesis of 4-[6,6-bis-(4-fluoro-phenyl)-hexanoyl]-piperazin-2-one

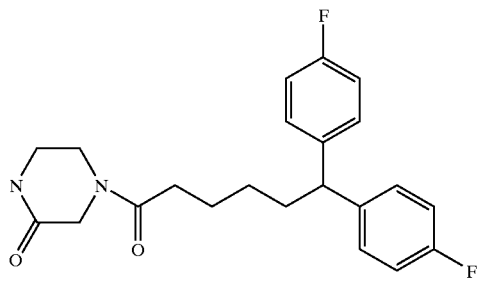

To a solution of 2-ketopiperazine (400 mg, 3.94 mmol) in dry $CH_2Cl_2$ (30 ml) was added 4,4'-difluorodiphenylhexanoic acid (1.0 g, 3.28 mmol) under nitrogen. To the reaction was added EDC (0.8 g, 4.26 mmol) and DMAP (cat) and the reaction mixture stirred under nitrogen at room temperature overnight. The reaction was then concentrated under reduced pressure. The residue dissolved in ethyl acetate:water (10:1) (80 ml). The organic was washed with water (20 ml, 2×) and 10% NaOH (20 ml) and dried over $MgSO_4$ and evaporated to dryness. The resulting residue was purified by column chromatography using $CH_2Cl_2$:MeOH (20:1) to give desired product in 62% yield.

C. Synthesis of 4-[6,6-bis-(4-fluoro-phenyl)-hexanoyl]-1-(3,4,5,-trimethoxy-benzyl)-piperazin-2-one (P48)

To a solution of 4-[6,6-bis-(4-fluoro-phenyl)-hexanoyl]-piperazin-2-one (0.5 g, 1.29 mmol) and trimethoxybenzyl bromide (337 mg, 1.29 mmol) in dry DMF (10 ml) was added NaH (60%, 60 mg, 1.48 mmol) under nitrogen. The mixture stirred at room temperature overnight, water (10 ml) was added and suspended solution was extracted with EtOAc (40 ml) and dried over $MgSO_4$. After evaporation and purification with column chromatography using $CH_2Cl_2$:MeOH (20:1) afforded the desired product in 63% yield.

EXAMPLE 8

Synthesis of 1-[6,6-bis-(4-fluoro-phenyl)-hexyl]-4-(3,4,5,-trimethoxy-benzyl)-piperazine-2-carboxylic acid ethyl ester (P36)

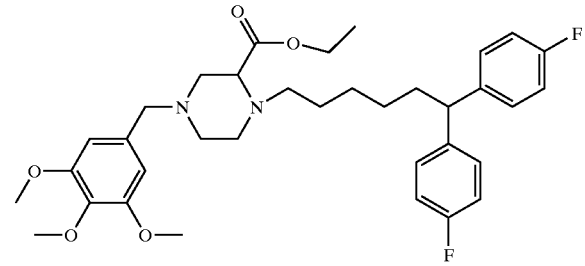

A. Synthesis of 1,4-Dibenzyl-piperazine-2-carboxylic acid ethyl ester

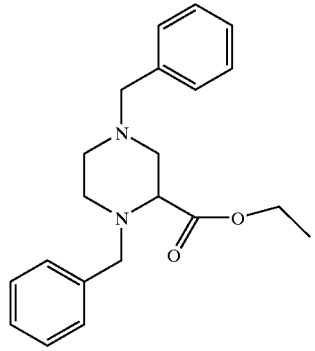

To a stirred solution of N,N'-dibenzyl-ethane-1,2-diamine (1 eq.) in anhydrous benzene was added triethylamine (2 eq.) and the mixture was heated to 40° C. under $N_2$. A solution of 2,3-dibromo-propionic acid ethyl ester (1 eq) in anhydrous benzene was added slowly and a dense white precipitate formed immediately. The mixture was heated at 80° C. for 3 h, cooled, filtered, and the filtrate washed with water, dried over $MgSO_4$, and evaporated under reduced pressure. The oil was purified by column chromatography on silica gel (Hexane:$Et_2O$ 4:1) for an 82% yield.

B. Synthesis of Piperazine 2- carboxylic acid ethyl ester

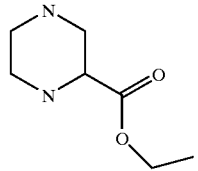

1,4-Dibenzyl-piperazine-2-carboxylic acid ethyl ester (1 eq.) was dissolved, with warming, in EtOH, and hydrogenated over 10% Pd—C at room temperature and atmospheric pressure until $H_2$ uptake ceased. The mixture was filtered through Celite and the solvent evaporated, giving an oil which was distilled under reduced pressure.

C. Synthesis of 4-(3,4,5-trimethoxy-benzyl)-piperazine-2-carboxylic acid ethyl ester

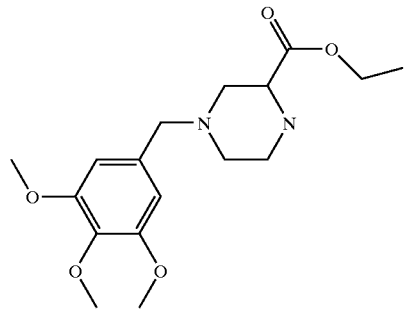

Piperazine 2-carboxylic acid ethyl ester (2.25 g, 14.25 mmol) was dissolved in dry benzene (30 ml) followed by addition of triehylamine (2.2 ml, 15.67 mmol). Trimethoxybenzyl bromide (3.72 g, 14.25 mmol) in dry benzene (30 ml) was added dropwise. The resulting mixture was stirred under nitrogen at room temperature overnight. The resulting salt was removed through filtration and solvent was evaporated. The crude product was purified by column chromatography using $CH_2Cl_2$:MeOH (15:1) to give the desired product in 44% yield.

D. Synthesis of 1-[6,6-bis-(4-fluoro-phenyl)-hexyl]-4-(3,4,5,-trimethoxy-benzyl)-piperazine-2-carboxylic acid ethyl ester (P36)

4-(3,4,5-trimethoxy-benzyl)-piperazine-2-carboxylic acid ethyl ester (2.0 g, 5.91 mmol) was dissolved in dry benzene (30 ml) followed by addition of triehylamine (0.65 g, 6.5 mmol) and resulting solution stirred for 1 hr. 1-[6,6-bis-(4-fluoro-phenyl)-hexyl bromide(2.08 g, 5.91 mmol) in dry benzene (30 ml) was added dropwise. The resulting mixture was stirred under nitrogen at room temperature overnight. The mixture was washed twice with water (30 ml) and dried over $MgSO_4$ and evaporated. The crude product was purified by column chromatography using hexane:ethyl acetate (3:1) to give the desired product in 56% yield

EXAMPLE 9

Synthesis of 1-[6,6-bis-(4-fluoro-phenyl)-hexyl]-4-(3,4,5,-trimethoxy-benzyl-piperazine-2-carboxylic acid

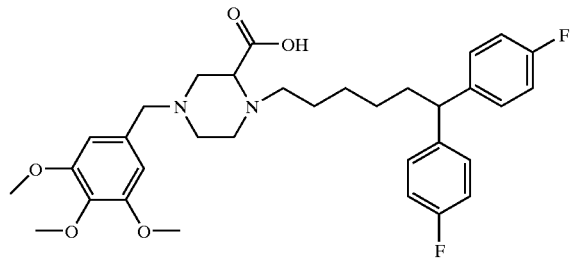

A mixture 1-[6,6-bis-(4-fluoro-phenyl)-hexyl]-4-(3,4,5,-trimethoxy-benzyl)-piperazine-2-carboxylic acid ethyl ester of (0.64 g, 1.04 mmol) and LiOH (132 mg, 3.14 mmol) in THF:MeOH:$H_2O$ (3:1:3, 35 ml) stirred at room temperature overnight. The solvent was then evaporated and residue dissolved in water (10 ml) and acidified with 2N HCl to pH 3. The aqueous phase was then extracted with EtOAc and organic phase was dried over $MgSO_4$. Purification by column chromatography using ($CH_2Cl_2$:MeOH 15:1) gave the desired product in 51% yield.

EXAMPLE 10

Assessment of Calcium Channel Blocking Activity

Antagonist activity was measured using whole cell patch recordings on human embryonic kidney cells either stably or transiently expressing rat N-type channels ($\alpha_{1B}$+$\alpha_{2b}$+$\beta_{1b}$ subunits) with 5 mM barium as a charge carrier. Alternatively, cells either stably or transiently expressing rat L-type channels ($\alpha_{1C}$+$\alpha_{2\delta}$+$\beta_{1b}$ cDNA subunits) and P/Q-type channels ($\alpha_{1A}$+$\alpha_{2\delta}$+$\beta_{1b}$ cDNA subunits).

For transient expression, host cells, such as human embryonic kidney cells, HEK 293 (ATCC# CRL 1573) were grown in standard DMEM medium supplemented with 2 mM glutamine and 10% fetal bovine serum. HEK 293 cells were transfected by a standard calcium-phosphate-DNA coprecipitation method using the rat $\alpha_{1B}$+$\beta_{1b}$+$\alpha_2\delta$ N-type calcium channel subunits in a vertebrate expression vector (for example, see *Current Protocols in Molecular Biology*).

After an incubation period of from 24 to 72 hrs the culture medium was removed and replaced with external recording solution (see below). Whole cell patch clamp experiments were performed using an Axopatch 200B amplifier (Axon Instruments, Burlingame, Calif.) linked to an IBM compatible personal computer equipped with pCLAMP software. Borosilicate glass patch pipettes (Sutter Instrument Co., Novato, Calif.) were polished (Microforge, Narishige, Japan) to a resistance of about 4 MΩ when filled with cesium methanesulfonate internal solution (composition in MM: 109 $CsCH_3SO_4$, 4 $MgCl_2$, 9 EGTA, 9 HEPES, pH 7.2). Cells were bathed in 5 mM $Ba^{++}$ (in mM: 5 $BaCl_2$, 1 $MgCl_2$, 10 HEPES, 40 tetraethylammonium chloride, 10 glucose, 87.5 CsCl pH 7.2). Current data shown were elicited by a train of 100 ms test pulses at 0.066 Hz from −100 mV and/or −80 mV to various potentials (min. −20 mV, max. +30 mV). Drugs were perfused directly into the vicinity of the cells using a microperfusion system.

Normalized dose-response curves were fit (Sigmaplot 4.0, SPSS Inc., Chicago, Ill.) by the Hill equation to determine $IC_{50}$ values. Steady-state inactivation curves were plotted as the normalized test pulse amplitude following 5 s inactivating prepulses at +10 mV increments. Inactivation curves were fit (Sigmaplot 4.0) with the Boltzman equation, $I_{peak}$ (normalized)=$1/(1+\exp((V-V_h)z/25.6))$, where V and $V_h$ are the conditioning and half inactivation potentials, respectively, and z is the slope factor.

EXAMPLE 11

Additional Methods

The methods of Example 10 were followed with slight modifications as will be apparent from the description below.

A. Transformation of HEK cells:

N-type calcium channel blocking activity was assayed in human embryonic kidney cells, HEK 293, stably transfected with the rat brain N-type calcium channel subunits ($\alpha_{1B}$+$\alpha_{2\delta}$+$\beta_{1b}$ cDNA subunits). Alternatively, N-type calcium channels ($\alpha_{1B}$+$\alpha_{2\delta}$+$\beta_{1b}$ cDNA subunits), L-type channels ($\alpha_{1C}$+$\alpha_{2\delta}$+$\beta_{1b}$ cDNA subunits) and P/Q-type channels ($\alpha_{1A}$+$\alpha_{2\delta}$+$\beta_{1b}$ cDNA subunits) were transiently expressed in HEK 293 cells. Briefly, cells were cultured in Dulbecco's modified eagle medium (DMEM) supplemented with 10% fetal bovine serum, 200 U/ml penicillin and 0.2 mg/ml streptomycin at 37° C. with 5% $CO_2$. At 85% confluency cells were split with 0.25% trypsin/1 mM EDTA and plated at 10% confluency on glass coverslips. At 12 hours the medium was replaced and the cells transiently transfected using a standard calcium phosphate protocol and the appropriate calcium channel cDNAs. Fresh DMEM was supplied and the cells transferred to 28° C./5% $CO_2$. Cells were incubated for 1 to 2 days to whole cell recording.

B. Measurement of Inhibition:

Whole cell patch clamp experiments were performed using an Axopatch 200B amplifier (Axon Instruments, Burlingame, Calif.) linked to a personal computer equipped with pCLAMP software. The external and internal recording solutions contained, respectively, 5 mM $BaCl_2$, 1 mM $MgCl_2$, 10 mM HEPES, 40 mM TEACl, 10 mM glucose, 87.5 mM CsCl (pH 7.2) and 108 mM CsMS, 4 mM $MgCl_2$, 9 mM EGTA, 9 mM HEPES (pH 7.2). Currents were typically elicited from a holding potential of −80 mV to +10 mV using Clampex software (Axon Instruments). Typically, currents were first elicited with low frequency stimulation (0.03 Hz) and allowed to stabilize prior to application of the compounds. The compounds were then applied during the low frequency pulse trains for two to three minutes to assess tonic block, and subsequently the pulse frequency was increased to 0.2 Hz to assess frequency dependent block. Data were analyzed using Clampfit (Axon Instruments) and SigmaPlot 4.0 (Jandel Scientific).

EXAMPLE 12

Channel Blocking Activities of Various Invention Compounds

Figure 2:
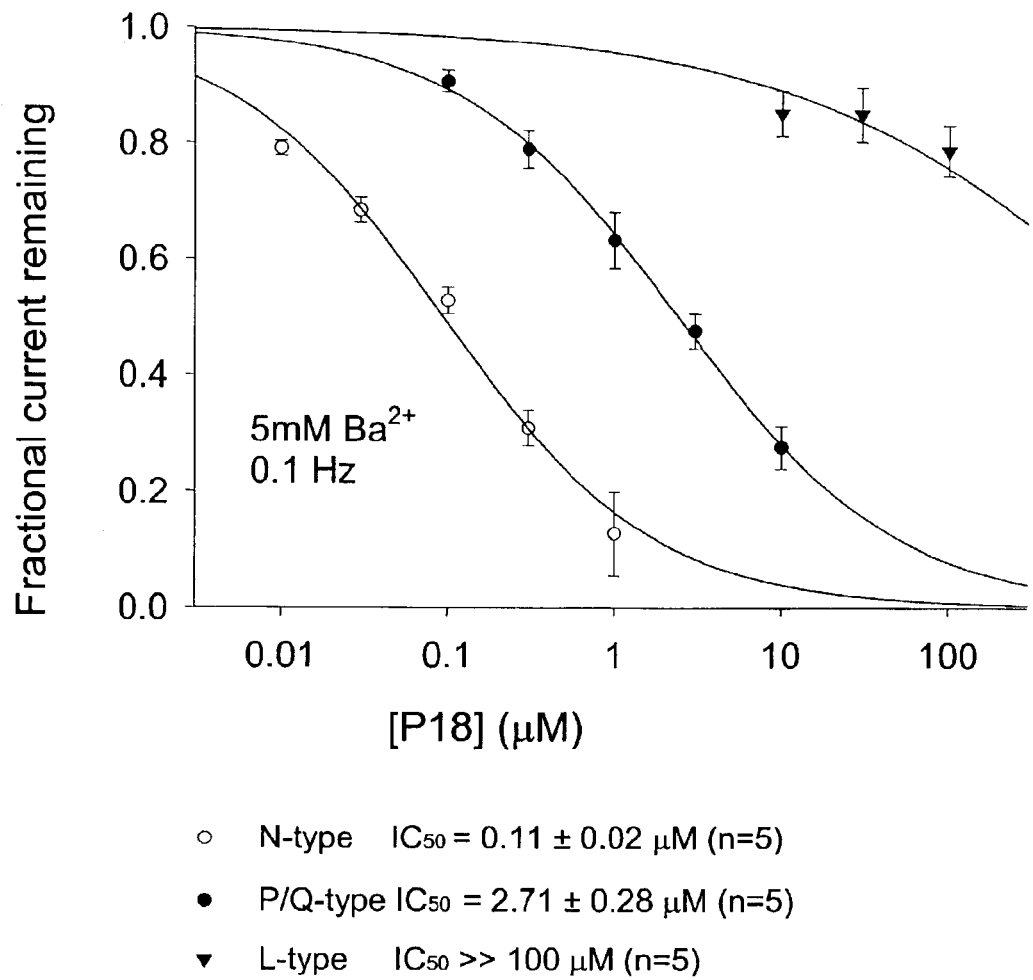
FIG. 2 is a graph showing the selectivity of compound P18 of the invention for N, PQ, T and L type channels.
Figure 3:
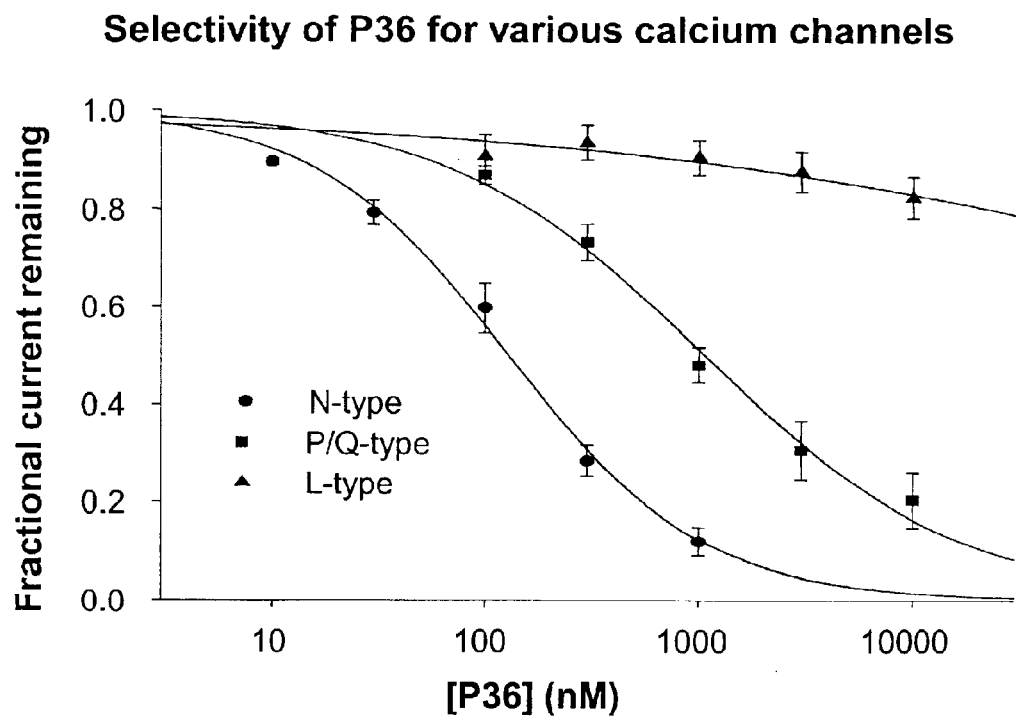
FIG. 3 is a graph showing the selectivity of compound P36 of the invention for N, PQ, T and L type channels.

Using the procedures set forth in Examples 10 and 11, various compounds of the invention were tested for their ability to block N-type calcium channels. The results show $IC_{50}$ values in the range of 0.05–1 μM in Table 1. In addition, FIGS. 2 and 3 show the specificities of compounds P18 and P36 which selectively block N-type channels as compared to L and P/Q-type.

TABLE 1

IC$_{50}$ Values for N-type Calcium Channel Block

| Compound | IC$_{50}$ (μM) (0.067 Hz) | IC$_{50}$ (μM) (0.2 Hz) |
|---|---|---|
| P1 | 0.125 | 0.060 |
| P2 | 0.113 | 0.071 |
| P3 | 0.119 | 0.089 |
| P4 | 0.150 | 0.090 |
| P5 | 0.169 | 0.091 |
| P6 | 0.200 | 0.093 |
| P7 | 0.168 | 0.109 |
| P8 | 0.445 | 0.168 |
| P9 | 0.436 | 0.259 |
| P10 | 0.399 | 0.267 |
| P11 | 0.525 | 0.270 |
| P12 | 0.430 | 0.280 |
| P13 | 0.370 | 0.310 |
| P14 | 0.480 | 0.340 |
| P15 | 0.599 | 0.354 |
| P16 | 0.082 | 0.041 |
| P17 | 0.062 | 0.044 |
| P18 | 0.147 | 0.089 |
| P19 | 0.191 | 0.098 |
| P20 | 0.132 | 0.100 |
| P21 | 0.184 | 0.105 |
| P22 | 0.346 | 0.134 |
| P23 | 0.182 | 0.134 |
| P24 | 0.181 | 0.142 |
| P25 | 0.275 | 0.147 |
| P26 | 0.302 | 0.175 |
| P27 | 0.242 | 0.192 |
| P28 | 0.379 | 0.217 |
| P29 | 0.356 | 0.297 |
| P30 | 0.748 | 0.354 |
| P31 | 0.122 | 0.101 |
| P32 | 0.345 | 0.245 |
| P33 | 0.362 | 0.257 |
| P34 | 0.337 | 0.268 |
| P35 | 0.403 | 0.296 |
| P36 | 0.240 | 0.130 |
| P37 | 0.179 | 0.141 |
| P38 | 0.251 | 0.157 |
| P39 | 0.280 | 0.173 |
| P40 | 0.286 | 0.214 |
| P41 | 0.364 | 0.236 |
| P42 | 0.380 | 0.240 |
| P43 | 0.312 | 0.250 |
| P44 | 0.280 | 0.180 |
| P45 | 0.575 | 0.334 |
| P46 | 0.430 | 0.340 |
| P47 | 0.420 | 0.290 |
| P48 | 0.102 | 0.056 |
| P49 | 0.61 | 0.41 |
| P50 | 0.26 | 0.19 |
| P51 | 0.15 | 0.085 |
| P52 | 0.40 | 0.37 |
| P53 | 0.20 | 0.98 |
| P54 | 0.12 | 0.076 |
| P55 | 0.19 | 0.15 |
| P56 | 0.078 | 0.059 |
| P57 | 0.60 | 0.40 |

EXAMPLE 13

Block of $\alpha_{1G}$ T-type Channels

Standard patch-clamp techniques were employed to identify blockers of T-type currents. Briefly, previously described HEK cell lines stably expressing human $\alpha_{1G}$ subunits were used for all the recordings (passage #: 4–20, 37° C., 5% $CO_2$). To obtain T-type currents, plastic dishes containing semi-confluent cells were positioned on the stage of a ZEISS AXIOVERT S100 microscope after replacing the culture medium with external solution (see below). Whole-cell patches were obtained using pipettes (borosilicate glass with filament, O.D.: 1.5 mm, I.D.: 0.86 mm, 10 cm length), fabricated on a SUTTER P-97 puller with resistance values of ~5 MΩ (see below for internal medium).

TABLE 2

External Solution 500 ml - pH 7.4, 265.5 mOsm

| Salt | Final mM | Stock M | Final ml |
|---|---|---|---|
| CsCl | 132 | 1 | 66 |
| CaCl$_2$ | 2 | 1 | 1 |
| MgCl$_2$ | 1 | 1 | 0.5 |
| HEPES | 10 | 0.5 | 10 |
| glucose | 10 | — | 0.9 grams |

TABLE 3

Internal Solution 50 ml - pH 7.3 with CsOH, 270 mOsm

| Salt | Final mM | Stock M | Final ml |
|---|---|---|---|
| Cs-Methanesulfonate | 108 | — | 1.231 gr/ 50 ml |
| MgCl$_2$ | 2 | 1 | 0.1 |
| HEPES | 10 | 0.5 | 1 |
| EGTA-Cs | 11 | 0.25 | 2.2 |
| ATP | 2 | 0.2 | 0.025 (1 aliquot/ 2.5 ml) |

T-type currents are reliably obtained by using two voltage protocols: "non-inactivating", and "inactivating"

In the non-inactivating protocol, the holding potential is set at −110 mV and with a pre-pulse at −100 mV for 1 second prior to the test pulse at 40 mV for 50 ms. In the inactivating protocol, the pre-pulse is at approximately −85 mV for 1 second, which inactivates about 15% of the T-type channels, as shown below.

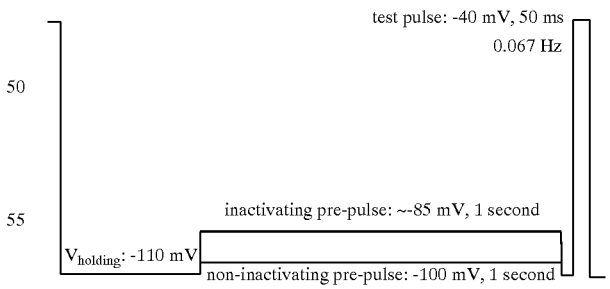

Test compounds were dissolved in external solution, 0.1–0.01% DMSO. After 10 min rest, they were applied by gravity close to the cell using a WPI microfil tubing. The "non-inactivating" pre-pulse was used to examine the resting block of a compound. The "inactivating" protocol was employed to study voltage-dependent block. However, the initial data were obtained using the non-inactivating protocol. IC$_{50}$ value of P18 was found to be 0.022 μM under this protocol.

What is claimed is:

1. A compound of the formula:

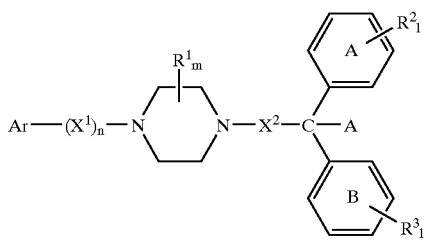

(1)

wherein Ar is phenyl, a six-membered or five-membered ring which is heteroaromatic or a fused aromatic or heteroaromatic system, each of which may optionally be substituted with one or more non-interfering substituents;
$X^1$ is a linker containing 1–5 members;
n is 0 or 1;
each $R^1$–$R^3$ is independently a non-interfering non-hydrogen substituent;
each l is independently 0–5;
m is 0–4;
$X^2$ is a linker comprising a chain of at least 5 members;
A is H, OR, SR, $NR_2$, or halo wherein R is H or lower alkyl (1–6C);
wherein phenyl rings A and B may optionally be linked by one or more $CR_2$ moieties wherein each R is H or lower alkyl (1–6C) wherein one or more of said $CR_2$ may be replaced by NR, O or S;
with the proviso that
(a) Ar is a five- or six-membered heteroaryl substituent or an optionally substituted fused aromatic or heteroaromatic substituent; and/or
(b) n is 0 and Ar is not unsubstituted phenyl; and/or
(c) m is 1–4 wherein if m is 1, R is =O, a carboxylic acid or a carboxylic ester; and/or
(d) $X^2$ is alkylene substituted by =O, OR, SR, $NR_2$ and/or halo and at least one l and/or m must be >0; and/or
(e) $X^2$ is a chain of at least 6 members; and/or
(f) $X^2$ contains at least one heteroatom selected from N, S and O; and/or
(g) A is OR, SR, $NR_2$ or halo, wherein R is H or lower alkyl (1–6C); and/or
(h) Ar is substituted with at least one t-butyl moiety or at least one substituted alkoxy; and/or
(i) $X^1$ includes at least one heteroatom not adjacent C=O selected from O, N and S; and/or
(j) $X^2$ is alkylene substituted by OR, SR, $NR_2$ and/or halo.

2. The compound of claim 1 which is of the formula

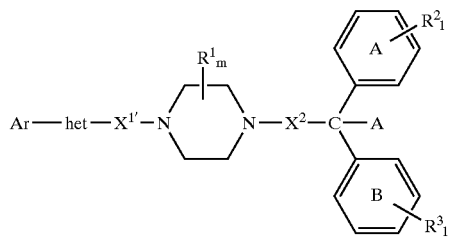

(2)

wherein Ar, $R^1$–$R^3$, l, m, $X^2$ and A are as defined above, "het" is a heteroatom selected from O, S and N, and wherein $X^1$ is defined as $X^1$ but lacking one chain member.

3. The compound of claim 1 which is of the formula

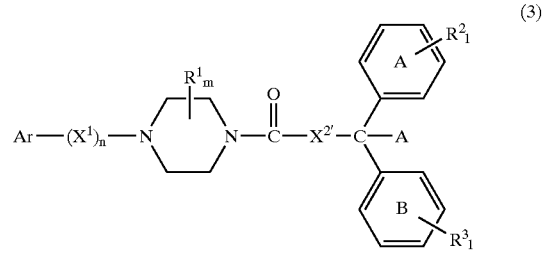

(3)

wherein Ar, $X^1$, $R^1$–$R^3$, l, m, n, A and Ar are defined as above, and $X^2$ is defined as $X^2$ but lacking one chain member.

4. The compound of claim 1 which is of the formula

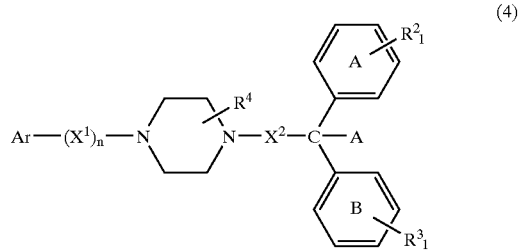

(4)

wherein $R^4$ is =O, or a carboxylic acid group or ester or amide thereof and Ar, $R^2$–$R^3$, $X^1$, l, n, $X^2$ and A are defined as above.

5. The compound of claim 1, wherein Ar is substituted and each non-interfering substituent is independently alkyl (1–10C), alkenyl (2–10C), alkynyl (2–10C), aryl (6–10C), arylalkyl (7–16C) or arylalkenyl (7–16C) each optionally further containing 1–4 heteroatoms (N, O or S) each further optionally substituted, or is independently =O, halo, $CF_3$, OCF, $NO_2$, $NH_2$, OH, or SH wherein S may optionally be oxidized.

6. The compound of claim 1, wherein the phenyl groups represented by A and B are linked by one or more $CR_2$ moieties wherein each R is H or lower alkyl (1–6C) wherein one or more of said $CR_2$ may be replaced by NR, O or S.

7. The compound of claim 1, wherein each l is independently 0 or 1.

8. The compound of claim 1, wherein $X^2$ is substituted by =O adjacent the piperazine ring.

9. The compound of claim 1, wherein n is 1 and $X^1$ is substituted by =O at the position next to the piperazine ring.

10. The compound of claim 1, wherein each of $R^2$ and $R^3$ is independently alkoxy, halo, or alkyl.

11. The compound of claim 1, wherein m is 1 and $R^1$ is =O or a carboxylic acid group or ester thereof.

12. The compound of claim 1, wherein Ar is optionally substituted phenyl.

13. The compound of claim 12, wherein said phenyl is unsubstituted or is substituted by one or more tert-butyl, methoxy, substituted alkoxy, hydroxy and/or halo.

14. The compound of claim 13, wherein the substituted alkoxy is substituted by an amino group.

15. The compound of claim 1, wherein Ar is optionally substituted pyrimidyl, pyridyl, benzothiazole, benzimidazole or indole.

16. A compound selected from the group consisting of
6,6-Bis-(4-fluoro-phenyl)-1-[4-(2-phenylsulfanyl-ethyl)-piperazin-1-yl]-hexan-1-one;
1-[6,6-Bis-(4-fluoro-phenyl)-hexyl]-4-[2-(4-fluoro-phenoxy)-ethyl]-piperazine;

1-{4-[2-(Benzo[1,3]dioxol-5-yloxy)-ethyl]-piperazin-1-yl}-6,6-bis-(4-fluoro-phenyl)-hexan-1-one;
1-[6,6-Bis-(4-fluoro-phenyl)-hexyl]-4-(2-phenylsulfanyl-ethyl)-piperazine;
1-[6,6-Bis-(4-fluoro-phenyl)-hexyl]-4-[2-(4-methoxy-phenoxy)-ethyl]-piperazine;
1-{4-[2-(2,4-Difluoro-phenoxy)-ethyl]-piperazin-1-yl}-6,6-bis-(4-fluoro-phenyl)-hexan-1-one;
6,6-Bis-(4-fluoro-phenyl)-1-[4-(2-phenoxy-ethyl)-piperazin-1-yl]-hexan-1-one;
1-{4-[2-(2,4-Dichloro-phenoxy)-ethyl]-piperazin-1-yl}-6,6-bis-(4-fluoro-phenyl)-hexan-1-one;
6,6-Bis-(4-fluoro-phenyl)-1-{4-[2-(4-methoxy-phenoxy)-ethyl]-piperazin-1-yl}-hexan-1-one;
1-[6,6-Bis-(4-fluoro-phenyl)-hexyl]-4-(2-phenoxy-ethyl)-piperazine;
6,6-Bis-(4-fluoro-phenyl)-1-{4-[2-(3,4,5-trimethoxy-phenoxy)-ethyl]-piperazin-1-yl}-hexan-1-one;
1-{4-[2-(Benzothiazol-2-ylsulfanyl)-ethyl]-piperazin-1-yl}-6,6-bis-(4-fluoro-phenyl)-hexan-1-one;
[4-(2-{4-[6,6-Bis-(4-fluoro-phenyl)-hexanoyl]-piperazin-1-yl}-ethoxy)-2,3,6-trimethyl-phenyl]-carbamic acid tert-butyl ester;
4-(2-{4-[6,6-Bis-(4-fluoro-phenyl)-hexyl]-piperazin-1-yl}-ethoxy)-2,3,6-trimethyl-phenylamine;
1-[6,6-Bis-(4-fluoro-phenyl)-hexyl]-4-[2-(2,4-dichloro-phenoxy)-ethyl]-piperazine;
[2-(4-{4-[6,6-Bis-(4-fluoro-phenyl)-hexyl]-piperazin-1-ylmethyl}-2,6-di-tert-butyl-phenoxy)-ethyl]-dimethyl-amine;
4-{4-[6,6-Bis-(4-fluoro-phenyl)-hexyl]-piperazin-1-ylmethyl}-2,6-di-tert-butyl-phenol;
1-[4-(3,5-Di-tert-butyl-4-methoxy-benzoyl)-piperazin-1-yl]-6,6-bis-(4-fluoro-phenyl)-hexan-1-one;
1-[4-(3,5-Di-tert-butyl-4-methoxy-benzyl)-piperazin-1-yl]-6,6-bis-(4-fluoro-phenyl)-hexan-1-one;
1-[6,6-Bis-(4-fluoro-phenyl)-hexyl]-4-(3,5-di-tert-butyl-4-methoxy-benzyl)-piperazine;
{4-[6,6-Bis-(4-fluoro-phenyl)-hexyl]-piperazin-1-yl}-(3,5-di-tert-butyl-4-methoxy-phenyl)-methanone;
1-{4-[3,5-Di-tert-butyl-4-(2-dimethylamino-ethoxy)-benzoyl]-piperazin-1-yl}-6,6-bis-(4-fluoro-phenyl)-hexan-1-one;
1-Benzo[1,3]dioxol-5-ylmethyl-4-[6,6-bis-(4-fluoro-phenyl)-hexyl]-piperazine;
1-[6,6-Bis-(4-fluoro-phenyl)-hexyl]-4-(3,5-di-tert-butyl-benzyl)-piperazine;
{4-[6,6-Bis-(4-fluoro-phenyl)-hexyl]-piperazin-1-yl}-(3,5-di-tert-butyl-4-hydroxy-phenyl)-methanone;
1-[4-(3,5-Di-tert-butyl-4-hydroxy-benzyl)-piperazin-1-yl]-6,6-bis-(4-fluoro-phenyl)-hexan-1-one;
1-[4-(3,5-Dibromo-4-hydroxy-benzoyl)-piperazin-1-yl]-6,6-bis-(4-fluoro-phenyl)-hexan-1-one;
1-[4-(3,5-Di-tert-butyl-4-hydroxy-benzoyl)-piperazin-1-yl]-6,6-bis-(4-fluoro-phenyl)-hexan-1-one;
1-[4-(3,5-Di-tert-butyl-benzoyl)-piperazin-1-yl]-6,6-bis-(4-fluoro-phenyl)-hexan-1-one;
1-[6,6-Bis-(4-fluoro-phenyl)-hexyl]-4-(4-tert-butyl-benzyl)-piperazine;
1-[6,6-Bis-(4-fluoro-phenyl)-hexyl]-4-(9H-thioxarithen-9-yl)-piperazine;
2-{4-[6,6-Bis-(4-fluoro-phenyl)-hexyl]-piperazin-1-yl}-benzothiazole;
6,6-Bis-(4-fluoro-phenyl)-1-(4-pyrimidin-2-yl-piperazin-1-yl)-hexan-1-one;
2-{4-[6,6-Bis-(4-fluoro-phenyl)-hexyl]-piperazin-1-yl}-pyrimidine;
6,6-Bis-(4-fluoro-phenyl)-1-[4-(9H-thioxanthen-9-yl)-piperazin-1-yl]-hexan-1-one;
1-[6,6-Bis-(4-fluoro-phenyl)-hexyl]-4-(3,4,5-trimethoxy-benzyl)-piperazine-2-carboxylic acid ethyl ester;
6,6-Bis-(4-fluoro-phenyl)-1-{4-[2-(3,4,5-trimethoxy-benzylamino)-ethyl]-piperazin-1-yl}-hexan-1-one;
9,9-Bis-(4-fluoro-phenyl)-1-[4-(3,4,5-trimethoxy-benzyl)-piperazin-1-yl]-nonan-1-one;
(2-{4-[6,6-Bis-(4-fluoro-phenyl)-hexyl]-piperazin-1-yl}-ethyl)-phenyl-amine;
1-[9,9-Bis-(4-fluoro-phenyl)-nonyl]-4-(3,4,5-trimethoxy-benzyl)-piperazine;
(4-{4-[Bis-(4-fluoro-phenyl)-methoxy]-butyl}-piperazin-1-yl)-(3,4,5-trimethoxy-phenyl)-methanone;
6,6-Bis-(4-fluoro-phenyl)-1-[4-(4-trifluoromethoxy-benzoyl)-piperazin-1-yl]-hexan-2-one;
1-[4-(4-Bromo-benzoyl)-piperazin-1-yl]-6,6-bis-(4-fluoro-phenyl)-hexan-1-one;
6,6-Bis-(4-fluoro-phenyl)-5-hydroxy-1-[4-(3,4,5-trimethoxy-benzoyl)-piperazin-1-yl]-hexan-1-one;
1-{4-[Bis-(4-fluoro-phenyl)-methoxy]-butyl}-4-(3,4,5-trimethoxy-benzyl)-piperazine;
6,6-Bis-(4-fluoro-phenyl)-6-hydroxy-1-[4-(3,4,5-trimethoxy-benzoyl)-piperazin-1-yl]-hexan-1-one;
4-[6,6-Bis-(4-fluoro-phenyl)-hexyl]-1-(3,4,5-trimethoxy-benzyl)-piperazine-2-carboxylic acid;
4-[6,6-Bis-(4-fluoro-phenyl)-hexanoyl]-1-(3,4,5-trimethoxy-benzyl)-piperazin-2-one;
1-[6,6-Bis-(4-fluoro-phenyl)-hexanoyl]-4-(3,5-di-tert-butyl-4-methoxy-benzoyl)-piperazin-2-one;
1-[6,6-Bis-(4-fluoro-phenyl)-hexyl]-4-(3,4,5-trimethoxy-benzoyl)-piperazin-2-one;
4-[6,6-Bis-(4-fluoro-phenyl)-hexyl]-1-(3,4,5-trimethoxy-benzoyl)-piperazin-2-one;
4-[6,6-Bis-(4-fluoro-phenyl)-hexanoyl]-1-(3,5-di-tert-butyl-4-methoxy-benzoyl)-piperazin-2-one;
4-[6,6-Bis-(4-fluoro-phenyl)-hexanoyl]-1-[2-(4-fluoro-phenoxy)-ethyl]-piperazin-2-one;
1-[6,6-Bis-(4-fluoro-phenyl)-hexyl]-4-(3,5-di-tert-butyl-4-methoxy-benzoyl)-piperazin-2-one;
4-[6,6-Bis-(4-fluoro-phenyl)-hexanoyl]-1-(3,5-di-tert-butyl-4-methoxy-benzyl)-piperazin-2-one;
1-[6,6-Bis-(4-fluoro-phenyl)-hexyl]-4-(3,5-di-tert-butyl-4-methoxy-benzyl)-piperazin-2-one;
1-[6,6-Bis-(4-fluoro-phenyl)-hexanoyl]-4-(3,5-di-tert-butyl-4-hydroxy-benzoyl)-piperazin-2-one;
6,6-Bis-(4-fluoro-phenyl)-1-[4-(3,4,5-trimethoxy-benzoyl)-piperazin-1-yl]-hex-5-en-1-one;
1-{4-[2-(3,4-Dimethoxy-phenoxy)-ethyl]-piperazin-1-yl}-6,6-bis-(4-fluoro-phenyl)-hexan-1-one; or
1-[6,6-Bis-(4-fluoro-phenyl)-hexyl]-4-[2-(3,4-dimethoxy-phenoxy)-ethyl]-piperazine.

17. A compound of claim 1 wherein Ar is a five- or six-membered heteroaryl substituent or an optionally substituted fused aromatic or heteroaromatic substituent; and wherein n is 0.

18. A compound of claim 1 wherein m is 1–4 wherein if m is 1, R is =O, a carboxylic acid or a carboxylic ester; and wherein $X^2$ is alkylene substituted by =O, OR, SR, $NR_2$ and/or halo.

19. A compound of claim 1 wherein $X^2$ is a chain of at least 6 members; and
 wherein $X^2$ contains at least one heteroatom selected from N, S and O.

20. A compound of claim 1 wherein A is OR, SR, $NR_2$ or halo, wherein R is H or lower alkyl (1–6C); and wherein Ar is substituted with at least one t-butyl moiety or at least one substituted alkoxy.

21. A compound of claim 1 wherein $X^1$ includes at least one heteroatom not adjacent C=O selected from O, N and S; and wherein $X^2$ is alkylene substituted by OR, SR, $NR_2$ and/or halo.

22. A pharmaceutical composition for use in treating conditions ameliorated by modulating calcium channel activity which composition comprises, in admixture with a pharmaceutically acceptable excipient, a unit dosage amount of at least one compound of claim 1.

23. A method to treat conditions ameliorated by modulating calcium channel activity in a subject which method comprises administering to a subject in need of such treatment at least one compound of claim 1 or a pharmaceutical composition thereof.

24. The method of claim 23 wherein said condition is a neurological disorder.

25. The method of claim 24 wherein said neurological disorder is stroke, anxiety, epilepsy, head trauma, migraine, chronic, neuropathic or acute pain, schizophrenia, depression or addiction.

26. The method of claim 25 wherein the condition is chronic, neuropathic or acute pain.

27. The method of claim 23 wherein the condition is a cardiovascular condition.

28. The method of claim 27 wherein said cardiovascular condition is hypertension or cardiac arrhythmia.

29. The method of claim 23 wherein the calcium channel activity is a T-type calcium channel activity and the condition is cancer, diabetes, infertility or sexual dysfunction.

* * * * *